US012584100B2

(12) United States Patent
Wei et al.

(10) Patent No.: US 12,584,100 B2
(45) Date of Patent: Mar. 24, 2026

(54) RECOMBINANT STRAIN FOR PRODUCING L-AMINO ACID, CONSTRUCTION METHOD THEREFOR, AND APPLICATION THEREOF

(71) Applicant: INNER MONGOLIA EPPEN BIOTECH CO., LTD., Inner Mongolia (CN)

(72) Inventors: Aiying Wei, Inner Mongolia (CN); Gang Meng, Inner Mongolia (CN); Xiaoqun Zhou, Inner Mongolia (CN); Chunguang Zhao, Inner Mongolia (CN); Fengyong Ma, Inner Mongolia (CN); Huiping Jia, Inner Mongolia (CN); Lipeng Yang, Inner Mongolia (CN); Houbo Su, Inner Mongolia (CN); Xiaowei Guo, Inner Mongolia (CN); Bin Tian, Inner Mongolia (CN); Xiaohang Gao, Inner Mongolia (CN)

(73) Assignee: INNER MONGOLIA EPPEN BIOTECH CO., LTD., Inner Mongolia (CN)

( * ) Notice: Subject to any disclaimer, the term of this patent is extended or adjusted under 35 U.S.C. 154(b) by 511 days.

(21) Appl. No.: 18/001,218

(22) PCT Filed: Dec. 31, 2020

(86) PCT No.: PCT/CN2020/142133
§ 371 (c)(1),
(2) Date: Dec. 8, 2022

(87) PCT Pub. No.: WO2021/248902
PCT Pub. Date: Dec. 16, 2021

(65) Prior Publication Data
US 2023/0313122 A1 Oct. 5, 2023

(30) Foreign Application Priority Data

Jun. 8, 2020 (CN) .......................... 202010514037.1
Aug. 7, 2020 (CN) .......................... 202010790887.4
Oct. 15, 2020 (CN) .......................... 202011105063.5

(51) Int. Cl.
| | |
|---|---|
| *C12N 15/77* | (2006.01) |
| *C12N 1/205* | (2026.01) |
| *C12P 13/04* | (2006.01) |
| *C12R 1/15* | (2006.01) |

(52) U.S. Cl.
CPC ............. *C12N 1/205* (2021.05); *C12N 15/77* (2013.01); *C12P 13/04* (2013.01); *C12R 2001/15* (2021.05)

(58) Field of Classification Search
CPC ...... C12N 15/77; C12N 1/205; C12N 9/1217; C12Y 207/02004; C12R 2001/15; C07K 14/34; C12P 13/04; C12P 13/08; C12P 13/14
See application file for complete search history.

(56) References Cited

U.S. PATENT DOCUMENTS 7,332,310 B2 2/2008 Nakagawa et al.

FOREIGN PATENT DOCUMENTS

| CN | 110951662 A | 4/2020 |
|---|---|---|
| CN | 111909944 A | 11/2020 |
| CN | 111961635 A | 11/2020 |

OTHER PUBLICATIONS

Devos et al., (Proteins: Structure, Function and Genetics, 2000, vol. 41: 98-107).*
Whisstock et al., (Quarterly Reviews of Biophysics 2003, vol. 36 (3): 307-340).*
Witowski et al., (Biochemistry 38:11643-11650, 1999).*
Kisselev L., (Structure, 2002, vol. 10: 8-9).*
Barker et al., "Mechanism of Regulation of Transcription Initiation by ppGpp. I. Effects of ppGpp on Transcription Initiation in Vivo and in Vitro", Journal of Molecular Biology, 305(4): 673-688 (2001).
International Search Report issued in International Application No. PCT/CN2020/142133, mailed on Apr. 1, 2021.
Wei et al., "L-Lysine From Metabolic Pathways to Industrial Production", Bulletin of Fermentation Science and Technology, 40(2): 31-34 (2011).

* cited by examiner

*Primary Examiner* — Jennifer E Graser
(74) *Attorney, Agent, or Firm* — JCIPRNET

(57) ABSTRACT
A bacterium for producing L-amino acid has improved expression of a polynucleotide encoding a protein represented by SEQ ID NO: 3 and improved expression of a polynucleotide encoding a protein represented by SEQ ID NO: 31, and/or has mutations in bases at positions -45 bp and -47 bp of a promotor region represented by SEQ ID NO: 57. A polynucleotide, encodes proteins and can be included in a recombinant vector, which can be included in a recombinant strain. These are useful in a method for producing L-amino acid. The polynucleotide encodes a protein which is represented by SEQ ID NO: 3 and has arginine at position 334 substituted by a terminator or encodes a protein which is represented by SEQ ID NO: 31 and has tyrosine at position 592 substituted by phenylalanine, or is formed by mutations in bases at positions -45 bp and -47 bp of a promotor region represented by SEQ ID NO:57.

9 Claims, No Drawings
Specification includes a Sequence Listing.

SEQUENCE LISTING

<160> NUMBER OF SEQ ID NOS: 64

<210> SEQ ID NO 1
<211> LENGTH: 1083
<212> TYPE: DNA
<213> ORGANISM: Corynebacterium glutamicum

<400> SEQUENCE: 1

```
gtgtcacaca ccgcgtccac accgacgcca gaggaatact ccgcgcagca acccagcacc      60
cagggcactc gcgttgagtt ccgcggcata accaaagtct ttagcaacaa taaatctgct     120
aaaaccaccg cgcttgataa tgtcactctc accgtagaac ccggtgaggt aatcggcatc     180
atcggttact ctggcgccgg caagtccact cttgtccgcc tcatcaatgg ccttgactcc     240
cccacgagcg gttcgttgct gctcaacggc accgacatcg tcggaatgcc cgagtctaag     300
ctgcgtaaac tgcgcagtaa tatcggcatg attttccagc agttcaacct gttccagtcg     360
cgtactgcgg ctggaaatgt ggagtacccg ctggaagttg ccaagatgga caaggcagct     420
cgtaaagctc gcgtgcaaga aatgctcgag ttcgtcggcc tgggcgacaa aggcaaaaac     480
taccccgagc agctgtcggg cggccagaag cagcgcgtcg gcattgcccg tgcactggcc     540
accaatccaa cgcttttgct tgccgacgaa gccacctccg ctttggaccc agaaaccacc     600
catgaagttc tggagctgct gcgcaaggta aaccgcgaac tgggcatcac catcgttgtg     660
atcacccacg aaatggaagt tgtgcgttcc atcgcagaca aggttgctgt gatggaatcc     720
ggcaaagttg tggaatacgg cagcgtctac gaggtgttct ccaatccaca aacacaggtt     780
gctcaaaagt tcgtggccac cgcgctgcgt aacaccccag accaagtgga atcggaagat     840
ctgcttagcc atgagggacg tctgttcacc attgatctga ctgaaacgtc cggcttcttt     900
gcagcaaccg ctcgtgctgc cgaacaaggt gcttttgtca acatcgttca cggtggcgtg     960
accaccttgc aacgccaatc atttggcaaa atgactgttc gactcaccgg caacaccgct    1020
gcgattgaag agttctatca aaccttgacc aagaccacga ccatcaagga gatcacccga    1080
tga                                                                  1083
```

<210> SEQ ID NO 2
<211> LENGTH: 1083
<212> TYPE: DNA
<213> ORGANISM: Artificial Sequence
<220> FEATURE:
<223> OTHER INFORMATION: NCgl0609R334* ORF sequence

<400> SEQUENCE: 2

```
gtgtcacaca ccgcgtccac accgacgcca gaggaatact ccgcgcagca acccagcacc      60
cagggcactc gcgttgagtt ccgcggcata accaaagtct ttagcaacaa taaatctgct     120
aaaaccaccg cgcttgataa tgtcactctc accgtagaac ccggtgaggt aatcggcatc     180
atcggttact ctggcgccgg caagtccact cttgtccgcc tcatcaatgg ccttgactcc     240
cccacgagcg gttcgttgct gctcaacggc accgacatcg tcggaatgcc cgagtctaag     300
ctgcgtaaac tgcgcagtaa tatcggcatg attttccagc agttcaacct gttccagtcg     360
cgtactgcgg ctggaaatgt ggagtacccg ctggaagttg ccaagatgga caaggcagct     420
cgtaaagctc gcgtgcaaga aatgctcgag ttcgtcggcc tgggcgacaa aggcaaaaac     480
```

-continued

```
taccccgagc agctgtcggg cggccagaag cagcgcgtcg gcattgcccg tgcactggcc      540
accaatccaa cgcttttgct tgccgacgaa gccacctccg ctttggaccc agaaaccacc      600
catgaagttc tggagctgct cgcaaggta aaccgcgaac tgggcatcac catcgttgtg      660
atcacccacg aaatggaagt tgtgcgttcc atcgcagaca aggttgctgt gatggaatcc      720
ggcaaagttg tggaatacgg cagcgtctac gaggtgttct ccaatccaca aacacaggtt      780
gctcaaaagt tcgtggccac cgcgctgcgt aacaccccag accaagtgga atcggaagat      840
ctgcttagcc atgagggacg tctgttcacc attgatctga ctgaaacgtc cggcttcttt      900
gcagcaaccg ctcgtgctgc cgaacaaggt gcttttgtca acatcgttca cggtggcgtg      960
accaccttgc aacgccaatc atttggcaaa atgactgttt gactcaccgg caacaccgct     1020
gcgattgaag agttctatca aaccttgacc aagaccacga ccatcaagga gatcacccga     1080
tga                                                                   1083
```

<210> SEQ ID NO 3
<211> LENGTH: 360
<212> TYPE: PRT
<213> ORGANISM: Corynebacterium glutamicum

<400> SEQUENCE: 3

```
Met Ser His Thr Ala Ser Thr Pro Thr Pro Glu Glu Tyr Ser Ala Gln
1               5                   10                  15

Gln Pro Ser Thr Gln Gly Thr Arg Val Glu Phe Arg Gly Ile Thr Lys
            20                  25                  30

Val Phe Ser Asn Asn Lys Ser Ala Lys Thr Thr Ala Leu Asp Asn Val
        35                  40                  45

Thr Leu Thr Val Glu Pro Gly Glu Val Ile Gly Ile Ile Gly Tyr Ser
    50                  55                  60

Gly Ala Gly Lys Ser Thr Leu Val Arg Leu Ile Asn Gly Leu Asp Ser
65                  70                  75                  80

Pro Thr Ser Gly Ser Leu Leu Leu Asn Gly Thr Asp Ile Val Gly Met
                85                  90                  95

Pro Glu Ser Lys Leu Arg Lys Leu Arg Ser Asn Ile Gly Met Ile Phe
            100                 105                 110

Gln Gln Phe Asn Leu Phe Gln Ser Arg Thr Ala Ala Gly Asn Val Glu
        115                 120                 125

Tyr Pro Leu Glu Val Ala Lys Met Asp Lys Ala Ala Arg Lys Ala Arg
    130                 135                 140

Val Gln Glu Met Leu Glu Phe Val Gly Leu Gly Asp Lys Gly Lys Asn
145                 150                 155                 160

Tyr Pro Glu Gln Leu Ser Gly Gly Gln Lys Gln Arg Val Gly Ile Ala
                165                 170                 175

Arg Ala Leu Ala Thr Asn Pro Thr Leu Leu Leu Ala Asp Glu Ala Thr
            180                 185                 190

Ser Ala Leu Asp Pro Glu Thr Thr His Glu Val Leu Glu Leu Leu Arg
        195                 200                 205

Lys Val Asn Arg Glu Leu Gly Ile Thr Ile Val Val Ile Thr His Glu
    210                 215                 220

Met Glu Val Val Arg Ser Ile Ala Asp Lys Val Ala Val Met Glu Ser
225                 230                 235                 240

Gly Lys Val Val Glu Tyr Gly Ser Val Tyr Glu Val Phe Ser Asn Pro
                245                 250                 255
```

```
Gln Thr Gln Val Ala Gln Lys Phe Val Ala Thr Ala Leu Arg Asn Thr
            260                 265                 270

Pro Asp Gln Val Glu Ser Glu Asp Leu Leu Ser His Glu Gly Arg Leu
            275                 280                 285

Phe Thr Ile Asp Leu Thr Glu Thr Ser Gly Phe Phe Ala Ala Thr Ala
            290                 295                 300

Arg Ala Ala Glu Gln Gly Ala Phe Val Asn Ile Val His Gly Gly Val
305                 310                 315                 320

Thr Thr Leu Gln Arg Gln Ser Phe Gly Lys Met Thr Val Arg Leu Thr
                325                 330                 335

Gly Asn Thr Ala Ala Ile Glu Glu Phe Tyr Gln Thr Leu Thr Lys Thr
            340                 345                 350

Thr Thr Ile Lys Glu Ile Thr Arg
            355                 360

<210> SEQ ID NO 4
<211> LENGTH: 333
<212> TYPE: PRT
<213> ORGANISM: Artificial Sequence
<220> FEATURE:
<223> OTHER INFORMATION: position 334 shown in SEQ ID NO: 3 is
      substituted by terminator

<400> SEQUENCE: 4

Met Ser His Thr Ala Ser Thr Pro Thr Pro Glu Glu Tyr Ser Ala Gln
1               5                   10                  15

Gln Pro Ser Thr Gln Gly Thr Arg Val Glu Phe Arg Gly Ile Thr Lys
            20                  25                  30

Val Phe Ser Asn Asn Lys Ser Ala Lys Thr Thr Ala Leu Asp Asn Val
            35                  40                  45

Thr Leu Thr Val Glu Pro Gly Glu Val Ile Gly Ile Ile Gly Tyr Ser
    50                  55                  60

Gly Ala Gly Lys Ser Thr Leu Val Arg Leu Ile Asn Gly Leu Asp Ser
65                  70                  75                  80

Pro Thr Ser Gly Ser Leu Leu Leu Asn Gly Thr Asp Ile Val Gly Met
                85                  90                  95

Pro Glu Ser Lys Leu Arg Lys Leu Arg Ser Asn Ile Gly Met Ile Phe
            100                 105                 110

Gln Gln Phe Asn Leu Phe Gln Ser Arg Thr Ala Ala Gly Asn Val Glu
            115                 120                 125

Tyr Pro Leu Glu Val Ala Lys Met Asp Lys Ala Ala Arg Lys Ala Arg
    130                 135                 140

Val Gln Glu Met Leu Glu Phe Val Gly Leu Gly Asp Lys Gly Lys Asn
145                 150                 155                 160

Tyr Pro Glu Gln Leu Ser Gly Gly Gln Lys Gln Arg Val Gly Ile Ala
                165                 170                 175

Arg Ala Leu Ala Thr Asn Pro Thr Leu Leu Leu Ala Asp Glu Ala Thr
            180                 185                 190

Ser Ala Leu Asp Pro Glu Thr Thr His Glu Val Leu Glu Leu Leu Arg
            195                 200                 205

Lys Val Asn Arg Glu Leu Gly Ile Thr Ile Val Val Ile Thr His Glu
    210                 215                 220

Met Glu Val Val Arg Ser Ile Ala Asp Lys Val Ala Val Met Glu Ser
225                 230                 235                 240
```

```
Gly Lys Val Val Glu Tyr Gly Ser Val Tyr Glu Val Phe Ser Asn Pro
            245                 250                 255

Gln Thr Gln Val Ala Gln Lys Phe Val Ala Thr Ala Leu Arg Asn Thr
            260                 265                 270

Pro Asp Gln Val Glu Ser Glu Asp Leu Leu Ser His Glu Gly Arg Leu
        275                 280                 285

Phe Thr Ile Asp Leu Thr Glu Thr Ser Gly Phe Phe Ala Ala Thr Ala
        290                 295                 300

Arg Ala Ala Glu Gln Gly Ala Phe Val Asn Ile Val His Gly Gly Val
305                 310                 315                 320

Thr Thr Leu Gln Arg Gln Ser Phe Gly Lys Met Thr Val
            325                 330
```

```
<210> SEQ ID NO 5
<211> LENGTH: 55
<212> TYPE: DNA
<213> ORGANISM: Artificial Sequence
<220> FEATURE:
<223> OTHER INFORMATION: Synthesized P1 primer

<400> SEQUENCE: 5
cagtgccaag cttgcatgcc tgcaggtcga ctctagggac ggcaacgtac ataac       55

<210> SEQ ID NO 6
<211> LENGTH: 29
<212> TYPE: DNA
<213> ORGANISM: Artificial Sequence
<220> FEATURE:
<223> OTHER INFORMATION: Synthesized P2 primer

<400> SEQUENCE: 6
gttgccggtg agtcaaacag tcattttgc                                    29

<210> SEQ ID NO 7
<211> LENGTH: 29
<212> TYPE: DNA
<213> ORGANISM: Artificial Sequence
<220> FEATURE:
<223> OTHER INFORMATION: Synthesized P3 primer

<400> SEQUENCE: 7
gcaaaatgac tgtttgactc accggcaac                                    29

<210> SEQ ID NO 8
<211> LENGTH: 56
<212> TYPE: DNA
<213> ORGANISM: Artificial Sequence
<220> FEATURE:
<223> OTHER INFORMATION: Synthesized P4 primer

<400> SEQUENCE: 8
cagctatgac catgattacg aattcgagct cggtacccgc ggctggaaat gtggag       56

<210> SEQ ID NO 9
<211> LENGTH: 18
<212> TYPE: DNA
<213> ORGANISM: Artificial Sequence
<220> FEATURE:
<223> OTHER INFORMATION: Synthesized P5 primer

<400> SEQUENCE: 9
ctagccggtt ccagtcag                                                18
```

-continued

<210> SEQ ID NO 10
<211> LENGTH: 19
<212> TYPE: DNA
<213> ORGANISM: Artificial Sequence
<220> FEATURE:
<223> OTHER INFORMATION: Synthesized P6 primer

<400> SEQUENCE: 10
ggacgtctgt tcaccattg                                               19

<210> SEQ ID NO 11
<211> LENGTH: 55
<212> TYPE: DNA
<213> ORGANISM: Artificial Sequence
<220> FEATURE:
<223> OTHER INFORMATION: Synthesized P7 primer

<400> SEQUENCE: 11
cagtgccaag cttgcatgcc tgcaggtcga ctctagaatg cgttctggac tgagg       55

<210> SEQ ID NO 12
<211> LENGTH: 55
<212> TYPE: DNA
<213> ORGANISM: Artificial Sequence
<220> FEATURE:
<223> OTHER INFORMATION: Synthesized P8 primer

<400> SEQUENCE: 12
cagtgccaag cttgcatgcc tgcaggtcga ctctagaatg cgttctggac tgagg       55

<210> SEQ ID NO 13
<211> LENGTH: 37
<212> TYPE: DNA
<213> ORGANISM: Artificial Sequence
<220> FEATURE:
<223> OTHER INFORMATION: Synthesized P9 primer

<400> SEQUENCE: 13
catctgttct cggtgcacca gctgcgagga tcatctc                           37

<210> SEQ ID NO 14
<211> LENGTH: 46
<212> TYPE: DNA
<213> ORGANISM: Artificial Sequence
<220> FEATURE:
<223> OTHER INFORMATION: Synthesized P10 primer

<400> SEQUENCE: 14
gatttaattg cgccatctga ttctggcaac aactccttcc ttgacc                 46

<210> SEQ ID NO 15
<211> LENGTH: 49
<212> TYPE: DNA
<213> ORGANISM: Artificial Sequence
<220> FEATURE:
<223> OTHER INFORMATION: Synthesized P11 primer

<400> SEQUENCE: 15
ggtcaaggaa ggagttgttg ccagaatcag atggcgcaat taaatcaag             49

<210> SEQ ID NO 16
<211> LENGTH: 60
<212> TYPE: DNA
<213> ORGANISM: Artificial Sequence
<220> FEATURE:
<223> OTHER INFORMATION: Synthesized P12 primer -continued

```
<400> SEQUENCE: 16
cagctatgac catgattacg aattcgagct cggtacccgc tatgacacct tcaacggatc      60

<210> SEQ ID NO 17
<211> LENGTH: 19
<212> TYPE: DNA
<213> ORGANISM: Artificial Sequence
<220> FEATURE:
<223> OTHER INFORMATION: Synthesized P13 primer

<400> SEQUENCE: 17
tccaaggaag atacacgcc                                                   19

<210> SEQ ID NO 18
<211> LENGTH: 18
<212> TYPE: DNA
<213> ORGANISM: Artificial Sequence
<220> FEATURE:
<223> OTHER INFORMATION: Synthesized P14 primer

<400> SEQUENCE: 18
cgaaatggaa gttgtgcg                                                    18

<210> SEQ ID NO 19
<211> LENGTH: 19
<212> TYPE: DNA
<213> ORGANISM: Artificial Sequence
<220> FEATURE:
<223> OTHER INFORMATION: Synthesized P15 primer

<400> SEQUENCE: 19
cgatgatgcc gattacctc                                                   19

<210> SEQ ID NO 20
<211> LENGTH: 18
<212> TYPE: DNA
<213> ORGANISM: Artificial Sequence
<220> FEATURE:
<223> OTHER INFORMATION: Synthesized P16 primer

<400> SEQUENCE: 20
cgttggaatc ttgcgttg                                                    18

<210> SEQ ID NO 21
<211> LENGTH: 55
<212> TYPE: DNA
<213> ORGANISM: Artificial Sequence
<220> FEATURE:
<223> OTHER INFORMATION: Synthesized P17 primer

<400> SEQUENCE: 21
gcttgcatgc ctgcaggtcg actctagagg atcccccagc tgcgaggatc atctc           55

<210> SEQ ID NO 22
<211> LENGTH: 54
<212> TYPE: DNA
<213> ORGANISM: Artificial Sequence
<220> FEATURE:
<223> OTHER INFORMATION: Synthesized P18 primer

<400> SEQUENCE: 22
atcaggctga aaatcttctc tcatccgcca aaaccaacaa ctccttcctt gacc            54

<210> SEQ ID NO 23
```

-continued

```
<211> LENGTH: 54
<212> TYPE: DNA
<213> ORGANISM: Artificial Sequence
<220> FEATURE:
<223> OTHER INFORMATION: Synthesized P19 primer

<400> SEQUENCE: 23
cagtgccaag cttgcatgcc tgcaggtcga ctctagaatg aatgggatgg gtcg          54

<210> SEQ ID NO 24
<211> LENGTH: 37
<212> TYPE: DNA
<213> ORGANISM: Artificial Sequence
<220> FEATURE:
<223> OTHER INFORMATION: Synthesized P20 primer

<400> SEQUENCE: 24
catcatcggt tactctggcc gaaatggaag ttgtgcg                             37

<210> SEQ ID NO 25
<211> LENGTH: 37
<212> TYPE: DNA
<213> ORGANISM: Artificial Sequence
<220> FEATURE:
<223> OTHER INFORMATION: Synthesized P21 primer

<400> SEQUENCE: 25
cgcacaactt ccatttcggc cagagtaacc gatgatg                             37

<210> SEQ ID NO 26
<211> LENGTH: 58
<212> TYPE: DNA
<213> ORGANISM: Artificial Sequence
<220> FEATURE:
<223> OTHER INFORMATION: Synthesized P22 primer

<400> SEQUENCE: 26
cagctatgac catgattacg aattcgagct cggtacccca acaactcctt ccttgacc      58

<210> SEQ ID NO 27
<211> LENGTH: 18
<212> TYPE: DNA
<213> ORGANISM: Artificial Sequence
<220> FEATURE:
<223> OTHER INFORMATION: Synthesized P23 primer

<400> SEQUENCE: 27
aatgaatggg atgggtcg                                                  18

<210> SEQ ID NO 28
<211> LENGTH: 20
<212> TYPE: DNA
<213> ORGANISM: Artificial Sequence
<220> FEATURE:
<223> OTHER INFORMATION: Synthesized P24 primer

<400> SEQUENCE: 28
caacaactcc ttccttgacc                                                20

<210> SEQ ID NO 29
<211> LENGTH: 2679
<212> TYPE: DNA
<213> ORGANISM: Corynebacterium glutamicum
```

-continued

<400> SEQUENCE: 29

```
atggcagaat caaacgctat ggaccgggca caaatctctg cactgctaga tagagcacag      60
cacacaatca accttgccga acaagcaaac aacgtgctcc gactgttgaa aacacccgga     120
acggccacag tagggggacaa cgggacactc ggcaccgata cctatctgat cccatcccgc     180
aacatcacct ggcctgacaa cctgtatgtc aacgtctttc tagacggcat gaatgcagaa     240 gccacccttta ccgattacgt cgcatcagtc gcttcgatcc cacgcctatg ccagatcatc     300
aacgagggcc aaggcggcat gttccgcaga ctattcaacc ccaccaaggt ccaagccggc     360
gaccaagctg tcttcgacct catggtcaaa ctcgacgaga tttcatctac cacccacgaa     420
gtctcccgca tgctcgaggg cgtccacgct gcccgcaccc gccaacaaca aggcgttgca     480
cttttcccag gtattcatgg agtgggggagag cgctacatcg aacgcgcaca acaggtactc     540
gcctcagccc tcggtatcgc tggattcggt gccgaaccct gggacggaca taccccttgcc     600 caagcgcgcc gggtagtcca acgctacgcc caagatccta actccgaata ccggctgaaa     660
agcgaagccg agaaacacct cacatccatc aacgagctcc gcgtacagat actcctcgaa     720
caactccccg ttgatgccct acgcatggct accgaccacc gcctgcgctt tggatccctc     780
gattccatcc acgtcgcaac cgtcgccgac gtcctaaaaa cacacacctc catcctcacc     840
accgtgcaag gtatcggcgc ccaaaccgcg gggcggatga aagccgcagc agaaacactc     900
aaacaagaag cactacgccg ccaaaacacc tccatcggcg acgaacctac ccaacccgcc     960
atgcgtctaa tcaacgtgct ggcccgcttc gaccaaaccg aaaccatcac gcccgaagaa    1020
cgcgcccgcc gcacccgcgt catcgactac gtagaacaca taccccccaag cctcgacccc    1080 tacatcgtca tcaacccagc aacgcctgag ttcaacaact tcaccgacga cctccgctgg    1140
atcgacgcaa accccaacct cttccaccca caaacaatca ccaccccacc cgccgacatc    1200
tgggacgact acatctcccg tcccgctcac taccaaggcc tgctagccac gctgctcggc    1260
cgcgacatcg aaggcgcaga cgaactcctc gacgccacca ccctccaaaa aatcagagac    1320 ctcacccctcg acaaaactca tctcaccgac ctccacctcc gcggatacca atcattcggc    1380
gcccgcttcg ccatcatcca aaagaaaacc ctcctcggcg acgacatggg actcggcaaa    1440
acagtccaag ccctctccgc agctgcacac cttgccgcca ccgaaaaaga cttccgcacc    1500
ctcgtcgtcg taccccgcatc cgtcattgtt aactggaccc gcgaatgcaa acgcttcctc    1560
aacctccccg tattcatcgc ccacggagac aacaaacaag acgccatcaa cgcctggtct    1620
aacaccaacg gaatcgcaat ctgcacctac gacggcgtcc gcaccatgga catccccgcg    1680
ccgggtctgg tcattgccga tgaagcccac ctgatcaaaa acccctccac caaacgcacc    1740
caagcactgc gcaaacttat cgacgccgcc ccatacaccc ttctgatgac cggcacacca    1800
ctagaaaaca aagtggaaga gtttgtaaat ctcgtgcgct acatccaacc ggagctgatc    1860 accccgtggca tgtccaaaat gcaggccgag aatttccgcg agcgcatcgc accagcctat    1920
ctgcgcagaa atcaagctga tgtgcttgac gaactcccag agcgcaccga ctccatcgac    1980
tggatcgacc tcaccccccaga agaccgcagc gcctacgacg accaagtccg ccaaggcagc    2040
tggatgggca tgcgccgctc cgccatgctc tcaccaacac cacgcctaac ttccgcaaaa    2100
atgcaacgca tcctagaact cttcgaagaa gcagaagaac acggccgcaa agccctcatc    2160
ttcacctact tcctcgacgt cctcgacgaa ctggaaaagc atctaggcga gcgcgtcatc    2220
ggccgcattt ccggcgacgt gccagccacc aagcgccaat tgcttgtcga cgccctgtcc    2280
```

-continued

```
cactccaaac ccggatccgc cctcattgcc caaatcaccg ccggggggagt aggcctaaac    2340 atccaatccg cgagcctatg cattatttgt gaacctcaag taaagccaac catcgaacag    2400
caggccgtcg cccgagtcca ccgcatgggc caaaccgcca ccgtccaagt ccaccgactc    2460
atcggcgacg aaaccgcaga cgaacgcatg ctagaaatcc tggcaggcaa aactcacgtc    2520
ttcgacgtct acgcccggct atctgaaacc gcagagattc cagatgctgt ggatatcact    2580
gaatcacagc tggcagcacg ggttattgat gaggagcgtg cacggttagg gcttactgaa    2640
tccactggcc ctaaagatga agaaacggcc ttaagctag                           2679

<210> SEQ ID NO 30
<211> LENGTH: 2679
<212> TYPE: DNA
<213> ORGANISM: Artificial Sequence
<220> FEATURE:
<223> OTHER INFORMATION: NCgl1575A1775T ORF sequence

<400> SEQUENCE: 30
atggcagaat caaacgctat ggaccgggca caaatctctg cactgctaga tagagcacag      60
cacacaatca accttgccga acaagcaaac aacgtgctcc gactgttgaa aacacccgga     120
acggccacag taggggacaa cgggacactc ggcaccgata cctatctgat cccatcccgc     180
aacatcacct ggcctgacaa cctgtatgtc aacgtctttc tagacggcat gaatgcagaa     240
gccaccctta ccgattacgt cgcatcagtc gcttcgatcc cacgcctatg ccagatcatc     300
aacgagggcc aaggcggcat gttccgcaga ctattcaacc ccaccaaggt ccaagccggc     360
gaccaagctg tcttcgacct catggtcaaa ctcgacgaga tttcatctac cacccacgaa     420
gtctcccgca tgctcgaggg cgtccacgct gcccgcaccc gccaacaaca aggcgttgca     480
cttttcccag gtattcatgg agtggggagag cgctacatcg aacgcgcaca acaggtactc     540
gcctcagccc tcggtatcgc tggattcggt gccgaaccct gggacggaca tacccttgcc     600
caagcgcgcc gggtagtcca acgctacgcc caagatccta actccgaata ccggctgaaa     660
agcgaagccg agaaacacct cacatccatc aacgagctcc gcgtacagat actcctcgaa     720
caactccccg ttgatgccct acgcatggct accgaccacc gcctgcgctt tggatccctc     780
gattccatcc acgtcgcaac cgtcgccgac gtcctaaaaa cacacacctc catcctcacc     840
accgtgcaag gtatcggcgc ccaaaccgcg gggcggatga aagccgcagc agaaacactc     900
aaacaagaag cactacgccg ccaaaacacc tccatcggcg acgaacctac ccaacccgcc     960
atgcgtctaa tcaacgtgct ggcccgcttc gaccaaaccg aaaccatcac gcccgaagaa    1020 cgcgccgcc gcaccgcgt catcgactac gtagaacaca taccccccaag cctcgacccc    1080 tacatcgtca tcaacccagc aacgcctgag ttcaacaact tcaccgacga cctccgctgg    1140
atcgacgcaa accccaacct cttccaccca caaacaatca ccaccccacc cgccgacatc    1200
tgggacgact acatctcccg tcccgctcac taccaaggcc tgctagccac gctgctcggc    1260
cgcgacatcg aaggcgcaga cgaactcctc gacgccacca ccctccaaaa aatcagagac    1320
ctcaccctcg acaaaactca tctcaccgac ctccacctcc gcggatacca atcattcggc    1380
gcccgcttcg ccatcatcca aaagaaaacc ctcctcggcg acgacatggg actcggcaaa    1440
acagtccaag ccctctccgc agctgcacac cttgccgcca ccgaaaaaga cttccgcacc    1500
ctcgtcgtcg tacccgcatc cgtcattgtt aactggaccc gcgaatgcaa acgcttcctc    1560
aacctccccg tattcatcgc ccacggagac aacaaacaag acgccatcaa cgcctggtct    1620
aacaccaacg gaatcgcaat ctgcacctac gacggcgtcc gcaccatgga catccccgcg    1680
```

-continued

```
ccgggtctgg tcattgccga tgaagcccac ctgatcaaaa acccctccac caaacgcacc    1740
caagcactgc gcaaacttat cgacgccgcc ccattcaccc ttctgatgac cggcacacca    1800
ctagaaaaca aagtggaaga gtttgtaaat ctcgtgcgct acatccaacc ggagctgatc    1860
acccgtggca tgtccaaaat gcaggccgag aatttccgcg agcgcatcgc accagcctat    1920
ctgcgcagaa atcaagctga tgtgcttgac gaactcccag agcgcaccga ctccatcgac    1980
tggatcgacc tcaccccaga agaccgcagc gcctacgacg accaagtccg ccaaggcagc    2040
tggatgggca tgcgccgctc cgccatgctc tcaccaacac cacgcctaac ttccgcaaaa    2100
atgcaacgca tcctagaact cttcgaagaa gcagaagaac acggccgcaa agccctcatc    2160
ttcacctact tcctcgacgt cctcgacgaa ctggaaaagc atctaggcga gcgcgtcatc    2220
ggccgcattt ccggcgacgt gccagccacc aagcgccaat tgcttgtcga cgccctgtcc    2280
cactccaaac ccggatccgc cctcattgcc caaatcaccg ccgggggagt aggcctaaac    2340
atccaatccg cgagcctatg cattatttgt gaacctcaag taaagccaac catcgaacag    2400
caggccgtcg cccgagtcca ccgcatgggc caaaccgcca ccgtccaagt ccaccgactc    2460
atcggcgacg aaaccgcaga cgaacgcatg ctagaaatcc tggcaggcaa aactcacgtc    2520
ttcgacgtct acgcccggct atctgaaacc gcagagattc cagatgctgt ggatatcact    2580
gaatcacagc tggcagcacg ggttattgat gaggagcgtg cacggttagg gcttactgaa    2640
tccactggcc ctaaagatga agaaacggcc ttaagctag                          2679
```

```
<210> SEQ ID NO 31
<211> LENGTH: 892
<212> TYPE: PRT
<213> ORGANISM: Corynebacterium glutamicum

<400> SEQUENCE: 31

Met Ala Glu Ser Asn Ala Met Asp Arg Ala Gln Ile Ser Ala Leu Leu
1               5                   10                  15

Asp Arg Ala Gln His Thr Ile Asn Leu Ala Glu Gln Ala Asn Asn Val
            20                  25                  30

Leu Arg Leu Leu Lys Thr Pro Gly Thr Ala Thr Val Gly Asp Asn Gly
        35                  40                  45

Thr Leu Gly Thr Asp Thr Tyr Leu Ile Pro Ser Arg Asn Ile Thr Trp
    50                  55                  60

Pro Asp Asn Leu Tyr Val Asn Val Phe Leu Asp Gly Met Asn Ala Glu
65                  70                  75                  80

Ala Thr Leu Thr Asp Tyr Val Ala Ser Val Ala Ser Ile Pro Arg Leu
                85                  90                  95

Cys Gln Ile Ile Asn Glu Gly Gln Gly Gly Met Phe Arg Arg Leu Phe
            100                 105                 110

Asn Pro Thr Lys Val Gln Ala Gly Asp Gln Ala Val Phe Asp Leu Met
        115                 120                 125

Val Lys Leu Asp Glu Ile Ser Ser Thr Thr His Glu Val Ser Arg Met
    130                 135                 140

Leu Glu Gly Val His Ala Ala Arg Thr Arg Gln Gln Gln Gly Val Ala
145                 150                 155                 160

Leu Phe Pro Gly Ile His Gly Val Gly Glu Arg Tyr Ile Glu Arg Ala
                165                 170                 175

Gln Gln Val Leu Ala Ser Ala Leu Gly Ile Ala Gly Phe Gly Ala Glu
            180                 185                 190
```

-continued

```
Pro Trp Asp Gly His Thr Leu Ala Gln Ala Arg Arg Val Gln Arg
        195                 200                 205

Tyr Ala Gln Asp Pro Asn Ser Glu Tyr Arg Leu Lys Ser Glu Ala Glu
        210                 215                 220

Lys His Leu Thr Ser Ile Asn Glu Leu Arg Val Gln Ile Leu Leu Glu
225                 230                 235                 240

Gln Leu Pro Val Asp Ala Leu Arg Met Ala Thr Asp His Arg Leu Arg
                245                 250                 255

Phe Gly Ser Leu Asp Ser Ile His Val Ala Thr Val Ala Asp Val Leu
                260                 265                 270

Lys Thr His Thr Ser Ile Leu Thr Thr Val Gln Gly Ile Gly Ala Gln
        275                 280                 285

Thr Ala Gly Arg Met Lys Ala Ala Glu Thr Leu Lys Gln Glu Ala
        290                 295                 300

Leu Arg Arg Gln Asn Thr Ser Ile Gly Asp Glu Pro Thr Gln Pro Ala
305                 310                 315                 320

Met Arg Leu Ile Asn Val Leu Ala Arg Phe Asp Gln Thr Glu Thr Ile
                325                 330                 335

Thr Pro Glu Glu Arg Ala Arg Arg Thr Arg Val Ile Asp Tyr Val Glu
                340                 345                 350

His Ile Pro Pro Ser Leu Asp Pro Tyr Ile Val Ile Asn Pro Ala Thr
        355                 360                 365

Pro Glu Phe Asn Asn Phe Thr Asp Asp Leu Arg Trp Ile Asp Ala Asn
        370                 375                 380

Pro Asn Leu Phe His Pro Gln Thr Ile Thr Thr Pro Pro Ala Asp Ile
385                 390                 395                 400

Trp Asp Asp Tyr Ile Ser Arg Pro Ala His Tyr Gln Gly Leu Leu Ala
                405                 410                 415

Thr Leu Leu Gly Arg Asp Ile Glu Gly Ala Asp Glu Leu Leu Asp Ala
                420                 425                 430

Thr Thr Leu Gln Lys Ile Arg Asp Leu Thr Leu Asp Lys Thr His Leu
        435                 440                 445

Thr Asp Leu His Leu Arg Gly Tyr Gln Ser Phe Gly Ala Arg Phe Ala
        450                 455                 460

Ile Ile Gln Lys Lys Thr Leu Leu Gly Asp Asp Met Gly Leu Gly Lys
465                 470                 475                 480

Thr Val Gln Ala Leu Ser Ala Ala Ala His Leu Ala Ala Thr Glu Lys
                485                 490                 495

Asp Phe Arg Thr Leu Val Val Val Pro Ala Ser Val Ile Val Asn Trp
                500                 505                 510

Thr Arg Glu Cys Lys Arg Phe Leu Asn Leu Pro Val Phe Ile Ala His
        515                 520                 525

Gly Asp Asn Lys Gln Asp Ala Ile Asn Ala Trp Ser Asn Thr Asn Gly
        530                 535                 540

Ile Ala Ile Cys Thr Tyr Asp Gly Val Arg Thr Met Asp Ile Pro Ala
545                 550                 555                 560

Pro Gly Leu Val Ile Ala Asp Glu Ala His Leu Ile Lys Asn Pro Ser
                565                 570                 575

Thr Lys Arg Thr Gln Ala Leu Arg Lys Leu Ile Asp Ala Ala Pro Tyr
                580                 585                 590

Thr Leu Leu Met Thr Gly Thr Pro Leu Glu Asn Lys Val Glu Glu Phe
        595                 600                 605
```

-continued

```
Val Asn Leu Val Arg Tyr Ile Gln Pro Glu Leu Ile Thr Arg Gly Met
    610             615             620

Ser Lys Met Gln Ala Glu Asn Phe Arg Glu Arg Ile Ala Pro Ala Tyr
625             630             635             640

Leu Arg Arg Asn Gln Ala Asp Val Leu Asp Glu Leu Pro Glu Arg Thr
            645             650             655

Asp Ser Ile Asp Trp Ile Asp Leu Thr Pro Glu Asp Arg Ser Ala Tyr
            660             665             670

Asp Asp Gln Val Arg Gln Gly Ser Trp Met Gly Met Arg Arg Ser Ala
            675             680             685

Met Leu Ser Pro Thr Pro Arg Leu Thr Ser Ala Lys Met Gln Arg Ile
    690             695             700

Leu Glu Leu Phe Glu Glu Ala Glu Glu His Gly Arg Lys Ala Leu Ile
705             710             715             720

Phe Thr Tyr Phe Leu Asp Val Leu Asp Glu Leu Glu Lys His Leu Gly
            725             730             735

Glu Arg Val Ile Gly Arg Ile Ser Gly Asp Val Pro Ala Thr Lys Arg
            740             745             750

Gln Leu Leu Val Asp Ala Leu Ser His Ser Lys Pro Gly Ser Ala Leu
            755             760             765

Ile Ala Gln Ile Thr Ala Gly Gly Val Gly Leu Asn Ile Gln Ser Ala
    770             775             780

Ser Leu Cys Ile Ile Cys Glu Pro Gln Val Lys Pro Thr Ile Glu Gln
785             790             795             800

Gln Ala Val Ala Arg Val His Arg Met Gly Gln Thr Ala Thr Val Gln
            805             810             815

Val His Arg Leu Ile Gly Asp Glu Thr Ala Asp Glu Arg Met Leu Glu
            820             825             830

Ile Leu Ala Gly Lys Thr His Val Phe Asp Val Tyr Ala Arg Leu Ser
            835             840             845

Glu Thr Ala Glu Ile Pro Asp Ala Val Asp Ile Thr Glu Ser Gln Leu
    850             855             860

Ala Ala Arg Val Ile Asp Glu Glu Arg Ala Arg Leu Gly Leu Thr Glu
865             870             875             880

Ser Thr Gly Pro Lys Asp Glu Glu Thr Ala Leu Ser
            885             890

<210> SEQ ID NO 32
<211> LENGTH: 892
<212> TYPE: PRT
<213> ORGANISM: Artificial Sequence
<220> FEATURE:
<223> OTHER INFORMATION: NCgl1575 Y592F coding protein sequence

<400> SEQUENCE: 32

Met Ala Glu Ser Asn Ala Met Asp Arg Ala Gln Ile Ser Ala Leu Leu
1               5               10              15

Asp Arg Ala Gln His Thr Ile Asn Leu Ala Glu Gln Ala Asn Asn Val
            20              25              30

Leu Arg Leu Leu Lys Thr Pro Gly Thr Ala Thr Val Gly Asp Asn Gly
        35              40              45

Thr Leu Gly Thr Asp Thr Tyr Leu Ile Pro Ser Arg Asn Ile Thr Trp
    50              55              60

Pro Asp Asn Leu Tyr Val Asn Val Phe Leu Asp Gly Met Asn Ala Glu
65              70              75              80
```

```
Ala Thr Leu Thr Asp Tyr Val Ala Ser Val Ala Ser Ile Pro Arg Leu
             85              90              95

Cys Gln Ile Ile Asn Glu Gly Gln Gly Gly Met Phe Arg Arg Leu Phe
            100             105             110

Asn Pro Thr Lys Val Gln Ala Gly Asp Gln Ala Val Phe Asp Leu Met
            115             120             125

Val Lys Leu Asp Glu Ile Ser Ser Thr Thr His Glu Val Ser Arg Met
    130             135             140

Leu Glu Gly Val His Ala Ala Arg Thr Arg Gln Gln Gln Gly Val Ala
145             150             155             160

Leu Phe Pro Gly Ile His Gly Val Gly Glu Arg Tyr Ile Glu Arg Ala
            165             170             175

Gln Gln Val Leu Ala Ser Ala Leu Gly Ile Ala Gly Phe Gly Ala Glu
            180             185             190

Pro Trp Asp Gly His Thr Leu Ala Gln Ala Arg Arg Val Val Gln Arg
            195             200             205

Tyr Ala Gln Asp Pro Asn Ser Glu Tyr Arg Leu Lys Ser Glu Ala Glu
    210             215             220

Lys His Leu Thr Ser Ile Asn Glu Leu Arg Val Gln Ile Leu Leu Glu
225             230             235             240

Gln Leu Pro Val Asp Ala Leu Arg Met Ala Thr Asp His Arg Leu Arg
            245             250             255

Phe Gly Ser Leu Asp Ser Ile His Val Ala Thr Val Ala Asp Val Leu
            260             265             270

Lys Thr His Thr Ser Ile Leu Thr Thr Val Gln Gly Ile Gly Ala Gln
            275             280             285

Thr Ala Gly Arg Met Lys Ala Ala Ala Glu Thr Leu Lys Gln Glu Ala
    290             295             300

Leu Arg Arg Gln Asn Thr Ser Ile Gly Asp Glu Pro Thr Gln Pro Ala
305             310             315             320

Met Arg Leu Ile Asn Val Leu Ala Arg Phe Asp Gln Thr Glu Thr Ile
            325             330             335

Thr Pro Glu Glu Arg Ala Arg Arg Thr Arg Val Ile Asp Tyr Val Glu
            340             345             350

His Ile Pro Pro Ser Leu Asp Pro Tyr Ile Val Ile Asn Pro Ala Thr
            355             360             365

Pro Glu Phe Asn Asn Phe Thr Asp Asp Leu Arg Trp Ile Asp Ala Asn
    370             375             380

Pro Asn Leu Phe His Pro Gln Thr Ile Thr Thr Pro Pro Ala Asp Ile
385             390             395             400

Trp Asp Asp Tyr Ile Ser Arg Pro Ala His Tyr Gln Gly Leu Leu Ala
            405             410             415

Thr Leu Leu Gly Arg Asp Ile Glu Gly Ala Asp Glu Leu Leu Asp Ala
            420             425             430

Thr Thr Leu Gln Lys Ile Arg Asp Leu Thr Leu Asp Lys Thr His Leu
            435             440             445

Thr Asp Leu His Leu Arg Gly Tyr Gln Ser Phe Gly Ala Arg Phe Ala
    450             455             460

Ile Ile Gln Lys Lys Thr Leu Leu Gly Asp Asp Met Gly Leu Gly Lys
465             470             475             480

Thr Val Gln Ala Leu Ser Ala Ala Ala His Leu Ala Ala Thr Glu Lys
            485             490             495
```

```
Asp Phe Arg Thr Leu Val Val Val Pro Ala Ser Val Ile Val Asn Trp
        500                 505                 510

Thr Arg Glu Cys Lys Arg Phe Leu Asn Leu Pro Val Phe Ile Ala His
        515                 520                 525

Gly Asp Asn Lys Gln Asp Ala Ile Asn Ala Trp Ser Asn Thr Asn Gly
        530                 535                 540

Ile Ala Ile Cys Thr Tyr Asp Gly Val Arg Thr Met Asp Ile Pro Ala
545                 550                 555                 560

Pro Gly Leu Val Ile Ala Asp Glu Ala His Leu Ile Lys Asn Pro Ser
                565                 570                 575

Thr Lys Arg Thr Gln Ala Leu Arg Lys Leu Ile Asp Ala Ala Pro Phe
        580                 585                 590

Thr Leu Leu Met Thr Gly Thr Pro Leu Glu Asn Lys Val Glu Glu Phe
        595                 600                 605

Val Asn Leu Val Arg Tyr Ile Gln Pro Glu Leu Ile Thr Arg Gly Met
        610                 615                 620

Ser Lys Met Gln Ala Glu Asn Phe Arg Glu Arg Ile Ala Pro Ala Tyr
625                 630                 635                 640

Leu Arg Arg Asn Gln Ala Asp Val Leu Asp Glu Leu Pro Glu Arg Thr
                645                 650                 655

Asp Ser Ile Asp Trp Ile Asp Leu Thr Pro Glu Asp Arg Ser Ala Tyr
                660                 665                 670

Asp Asp Gln Val Arg Gln Gly Ser Trp Met Gly Met Arg Arg Ser Ala
                675                 680                 685

Met Leu Ser Pro Thr Pro Arg Leu Thr Ser Ala Lys Met Gln Arg Ile
        690                 695                 700

Leu Glu Leu Phe Glu Glu Ala Glu Glu His Gly Arg Lys Ala Leu Ile
705                 710                 715                 720

Phe Thr Tyr Phe Leu Asp Val Leu Asp Glu Leu Glu Lys His Leu Gly
                725                 730                 735

Glu Arg Val Ile Gly Arg Ile Ser Gly Asp Val Pro Ala Thr Lys Arg
                740                 745                 750

Gln Leu Leu Val Asp Ala Leu Ser His Ser Lys Pro Gly Ser Ala Leu
        755                 760                 765

Ile Ala Gln Ile Thr Ala Gly Gly Val Gly Leu Asn Ile Gln Ser Ala
        770                 775                 780

Ser Leu Cys Ile Ile Cys Glu Pro Gln Val Lys Pro Thr Ile Glu Gln
785                 790                 795                 800

Gln Ala Val Ala Arg Val His Arg Met Gly Gln Thr Ala Thr Val Gln
                805                 810                 815

Val His Arg Leu Ile Gly Asp Glu Thr Ala Asp Glu Arg Met Leu Glu
        820                 825                 830

Ile Leu Ala Gly Lys Thr His Val Phe Asp Val Tyr Ala Arg Leu Ser
        835                 840                 845

Glu Thr Ala Glu Ile Pro Asp Ala Val Asp Ile Thr Glu Ser Gln Leu
        850                 855                 860

Ala Ala Arg Val Ile Asp Glu Glu Arg Ala Arg Leu Gly Leu Thr Glu
865                 870                 875                 880

Ser Thr Gly Pro Lys Asp Glu Glu Thr Ala Leu Ser
                885                 890
```

<210> SEQ ID NO 33
<211> LENGTH: 56
<212> TYPE: DNA

-continued

```
<213> ORGANISM: Artificial Sequence
<220> FEATURE:
<223> OTHER INFORMATION: Synthesized P1' primer

<400> SEQUENCE: 33
cagtgccaag cttgcatgcc tgcaggtcga ctctagtgcg ttcgtctgcg gtttcg          56

<210> SEQ ID NO 34
<211> LENGTH: 30
<212> TYPE: DNA
<213> ORGANISM: Artificial Sequence
<220> FEATURE:
<223> OTHER INFORMATION: Synthesized P2' primer

<400> SEQUENCE: 34
atcgacgccg ccccattcac ccttctgatg                                       30

<210> SEQ ID NO 35
<211> LENGTH: 30
<212> TYPE: DNA
<213> ORGANISM: Artificial Sequence
<220> FEATURE:
<223> OTHER INFORMATION: Synthesized P3' primer

<400> SEQUENCE: 35
catcagaagg gtgaatgggg cggcgtcgat                                       30

<210> SEQ ID NO 36
<211> LENGTH: 57
<212> TYPE: DNA
<213> ORGANISM: Artificial Sequence
<220> FEATURE:
<223> OTHER INFORMATION: Synthesized P4' primer

<400> SEQUENCE: 36
cagctatgac catgattacg aattcgagct cggtacccaa gcctcgaccc ctacatc         57

<210> SEQ ID NO 37
<211> LENGTH: 20
<212> TYPE: DNA
<213> ORGANISM: Artificial Sequence
<220> FEATURE:
<223> OTHER INFORMATION: Synthesized P5' primer

<400> SEQUENCE: 37
cacatcagct tgatttctgc                                                  20

<210> SEQ ID NO 38
<211> LENGTH: 20
<212> TYPE: DNA
<213> ORGANISM: Artificial Sequence
<220> FEATURE:
<223> OTHER INFORMATION: Synthesized P6' primer

<400> SEQUENCE: 38
ggtcattgcc gatgaagccc                                                  20

<210> SEQ ID NO 39
<211> LENGTH: 55
<212> TYPE: DNA
<213> ORGANISM: Artificial Sequence
<220> FEATURE:
<223> OTHER INFORMATION: Synthesized P7' primer

<400> SEQUENCE: 39
cagtgccaag cttgcatgcc tgcaggtcga ctctagaatg cgttctggac tgagg           55
```

```
<210> SEQ ID NO 40
<211> LENGTH: 36
<212> TYPE: DNA
<213> ORGANISM: Artificial Sequence
<220> FEATURE:
<223> OTHER INFORMATION: Synthesized P8' primer

<400> SEQUENCE: 40
gaaacggcct taagctaggt gcaccgagaa cagatg                          36

<210> SEQ ID NO 41
<211> LENGTH: 36
<212> TYPE: DNA
<213> ORGANISM: Artificial Sequence
<220> FEATURE:
<223> OTHER INFORMATION: Synthesized P9' primer

<400> SEQUENCE: 41
catctgttct cggtgcacct agcttaaggc cgtttc                          36

<210> SEQ ID NO 42
<211> LENGTH: 39
<212> TYPE: DNA
<213> ORGANISM: Artificial Sequence
<220> FEATURE:
<223> OTHER INFORMATION: Synthesized P10' primer

<400> SEQUENCE: 42
cttgatttaa ttgcgccatc aagcttttcc cgcccggtt                       39

<210> SEQ ID NO 43
<211> LENGTH: 39
<212> TYPE: DNA
<213> ORGANISM: Artificial Sequence
<220> FEATURE:
<223> OTHER INFORMATION: Synthesized P11' primer

<400> SEQUENCE: 43
aaccgggcgg gaaaagcttg atggcgcaat taaatcaag                       39

<210> SEQ ID NO 44
<211> LENGTH: 60
<212> TYPE: DNA
<213> ORGANISM: Artificial Sequence
<220> FEATURE:
<223> OTHER INFORMATION: Synthesized P12' primer

<400> SEQUENCE: 44
cagctatgac catgattacg aattcgagct cggtacccgc tatgacacct tcaacggatc   60

<210> SEQ ID NO 45
<211> LENGTH: 19
<212> TYPE: DNA
<213> ORGANISM: Artificial Sequence
<220> FEATURE:
<223> OTHER INFORMATION: Synthesized P13' primer

<400> SEQUENCE: 45
tccaaggaag atacacgcc                                             19

<210> SEQ ID NO 46
<211> LENGTH: 20
<212> TYPE: DNA
<213> ORGANISM: Artificial Sequence
<220> FEATURE:
```

<223> OTHER INFORMATION: Synthesized P14' primer

<400> SEQUENCE: 46
cttctgatga ccggcacacc                                           20

<210> SEQ ID NO 47
<211> LENGTH: 20
<212> TYPE: DNA
<213> ORGANISM: Artificial Sequence
<220> FEATURE:
<223> OTHER INFORMATION: Synthesized P15' primer

<400> SEQUENCE: 47
tagtcgatga cgcgggtgcg                                           20

<210> SEQ ID NO 48
<211> LENGTH: 18
<212> TYPE: DNA
<213> ORGANISM: Artificial Sequence
<220> FEATURE:
<223> OTHER INFORMATION: Synthesized P16' primer

<400> SEQUENCE: 48
cgttggaatc ttgcgttg                                             18

<210> SEQ ID NO 49
<211> LENGTH: 54
<212> TYPE: DNA
<213> ORGANISM: Artificial Sequence
<220> FEATURE:
<223> OTHER INFORMATION: Synthesized P17' primer

<400> SEQUENCE: 49
gcttgcatgc ctgcaggtcg actctagagg atccccctag cttaaggccg tttc     54

<210> SEQ ID NO 50
<211> LENGTH: 53
<212> TYPE: DNA
<213> ORGANISM: Artificial Sequence
<220> FEATURE:
<223> OTHER INFORMATION: Synthesized P18' primer

<400> SEQUENCE: 50
atcaggctga aaatcttctc tcatccgcca aaacaagctt ttcccgcccg gtt      53

<210> SEQ ID NO 51
<211> LENGTH: 56
<212> TYPE: DNA
<213> ORGANISM: Artificial Sequence
<220> FEATURE:
<223> OTHER INFORMATION: Synthesized P19' primer

<400> SEQUENCE: 51
cagtgccaag cttgcatgcc tgcaggtcga ctctagaccg gcgcagatgc caacgc   56

<210> SEQ ID NO 52
<211> LENGTH: 37
<212> TYPE: DNA
<213> ORGANISM: Artificial Sequence
<220> FEATURE:
<223> OTHER INFORMATION: Synthesized P20' primer

<400> SEQUENCE: 52
cccagaactg aaggtctaat tgcctaaggc cggaatt                        37

<210> SEQ ID NO 53
<211> LENGTH: 37
<212> TYPE: DNA
<213> ORGANISM: Artificial Sequence
<220> FEATURE:
<223> OTHER INFORMATION: Synthesized P21' primer

<400> SEQUENCE: 53
aattccggcc ttaggcaatt agaccttcag ttctggg                                        37

<210> SEQ ID NO 54
<211> LENGTH: 56
<212> TYPE: DNA
<213> ORGANISM: Artificial Sequence
<220> FEATURE:
<223> OTHER INFORMATION: Synthesized P22' primer

<400> SEQUENCE: 54
cagctatgac catgattacg aattcgagct cggtacccgc ttgatgaagg ctccag           56

<210> SEQ ID NO 55
<211> LENGTH: 20
<212> TYPE: DNA
<213> ORGANISM: Artificial Sequence
<220> FEATURE:
<223> OTHER INFORMATION: Synthesized P23' primer

<400> SEQUENCE: 55
accggcgcag atgccaacgc                                                           20

<210> SEQ ID NO 56
<211> LENGTH: 18
<212> TYPE: DNA
<213> ORGANISM: Artificial Sequence
<220> FEATURE:
<223> OTHER INFORMATION: Synthesized P24' primer

<400> SEQUENCE: 56
gcttgatgaa ggctccag                                                             18

<210> SEQ ID NO 57
<211> LENGTH: 242
<212> TYPE: DNA
<213> ORGANISM: Corynebacterium glutamicum

<400> SEQUENCE: 57
ttcagggtag ttgactaaag agttgctcgc gaagtagcac ctgtcacttt tgtctcaaat     60
attaaatcga atatcaatat atggtctgtt tattggaacg cgtcccagtg gctgagacgc    120
atccgctaaa gccccaggaa ccctgtgcag aaagaaaaca ctcctctggc taggtagaca    180
cagtttataa aggtagagtt gagcgggtaa ctgtcagcac gtagatcgaa aggtgcacaa    240
ag                                                                    242

<210> SEQ ID NO 58
<211> LENGTH: 242
<212> TYPE: DNA
<213> ORGANISM: Artificial Sequence
<220> FEATURE:
<223> OTHER INFORMATION: mutated promotor sequence

<400> SEQUENCE: 58
ttcagggtag ttgactaaag agttgctcgc gaagtagcac ctgtcacttt tgtctcaaat     60
attaaatcga atatcaatat atggtctgtt tattggaacg cgtcccagtg gctgagacgc    120

-continued

```
atccgctaaa gccccaggaa ccctgtgcag aaagaaaaca ctcctctggc taggtagaca      180
cagtttataa aggtataatt gagcgggtaa ctgtcagcac gtagatcgaa aggtgcacaa      240
ag                                                                     242

<210> SEQ ID NO 59
<211> LENGTH: 29
<212> TYPE: DNA
<213> ORGANISM: Artificial Sequence
<220> FEATURE:
<223> OTHER INFORMATION: Synthesized P1'' primer

<400> SEQUENCE: 59
ccggaattcg accaaggatg agggctttg                                         29

<210> SEQ ID NO 60
<211> LENGTH: 30
<212> TYPE: DNA
<213> ORGANISM: Artificial Sequence
<220> FEATURE:
<223> OTHER INFORMATION: Synthesized P2'' primer

<400> SEQUENCE: 60
agttacccgc tcaattatac ctttataaac                                        30

<210> SEQ ID NO 61
<211> LENGTH: 30
<212> TYPE: DNA
<213> ORGANISM: Artificial Sequence
<220> FEATURE:
<223> OTHER INFORMATION: Synthesized P3'' primer

<400> SEQUENCE: 61
gtttataaag gtataattga gcgggtaact                                        30

<210> SEQ ID NO 62
<211> LENGTH: 30
<212> TYPE: DNA
<213> ORGANISM: Artificial Sequence
<220> FEATURE:
<223> OTHER INFORMATION: Synthesized P4'' primer

<400> SEQUENCE: 62
acatgcatgc gcgtacgcga agtggcacat                                        30

<210> SEQ ID NO 63
<211> LENGTH: 20
<212> TYPE: DNA
<213> ORGANISM: Artificial Sequence
<220> FEATURE:
<223> OTHER INFORMATION: Synthesized P5'' primer

<400> SEQUENCE: 63
atcaatatat ggtctgttta                                                   20

<210> SEQ ID NO 64
<211> LENGTH: 20
<212> TYPE: DNA
<213> ORGANISM: Artificial Sequence
<220> FEATURE:
<223> OTHER INFORMATION: Synthesized P6'' primer

<400> SEQUENCE: 64
cttggtggca acgatccgtt                                                   20
```

RECOMBINANT STRAIN FOR PRODUCING L-AMINO ACID, CONSTRUCTION METHOD THEREFOR, AND APPLICATION THEREOF

The present application claimed the priorities of the Patent Application No. 202011105063.5 filed to State Intellectual Property Office of P.R.China on Oct. 15, 2020, entitled "A recombinant strain for producing L-amino acid, construction method therefor, and application thereof"; the Patent Application No. 202010790887.4 filed to State Intellectual Property Office of P.R. China on Aug. 7, 2020, entitled "A recombinant strain for producing L-amino acid, construction method therefor, and application thereof"; and the Patent Application No. 202010514037.1 filed to State Intellectual Property Office of P.R.China on Jun. 8, 2020, entitled "A recombinant strain for lysc gene modification, construction method therefor, and application thereof". The three prior applications are all incorporated herein by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SL_JEEK044_001APC.TXT, the date of creation of the ASCII text file is May 25, 2023, and the size of the ASCII text file is 43,910 bytes.

DEPOSIT OF MICROORGANISM

The following microorganism has been deposited in accordance with the terms of the Budapest Treaty with the China General Microbiological Culture Collection Center (CGMCC) on the date indicated:

| Microorganism | Accession No. | Date |
| --- | --- | --- |
| *Corynebacterium glutamicum* | CGMCC No. 12856 | Aug. 16, 2016 |

*Corynebacterium glutamicum* was deposited under Accession Number CGMCC No. 12856 on Aug. 16, 2016 with the China General Microbiological Culture Collection Center (CGMCC). This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by CGMCC under the terms of the Budapest Treaty, and subject to an agreement between Applicant and CGMCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14). Availability of the deposited strain is not to be construed as a license to practice the invention in contravention of the rights granted under the authority of any government in accordance with its patent laws.

TECHNICAL FIELD

The invention belongs to the field of genetic engineering and microbial technology, particularly relates to a recombinant strain producing L-amino acid, construction method therefor, and application thereof.

BACKGROUND

L-lysine has a wide range of applications, including medicine, food, feed, and other aspects. Among them, L-Lysine used as feed additive accounts for more than 90% of the total amount. At present, China is the second largest consumer market and the largest producer for L-lysine.

At present, L-lysine is mainly produced by direct fermentation, which uses strains with complete biosynthetic pathway of L-lysine and takes waste molasses, starch hydrolysate and the like as substrates to produce L-lysine via aerobic fermentation. This method accounts for 2/3 of the production of L-lysine all over the world today, and its process is very mature. This method mainly exists in yeast, bacteria and mold, and widely exists in microorganisms. At present, the production strains used for L-lysine fermentation in industry are mainly mutagenesis breeding mutant strains of *Corynebacterium* and *Brevibacterium* genus. With the development of metabolic engineering and genetic engineering, gene mutation became controllable. Therefore, in the process of engineering a starting strain with metabolic engineering, it is possible to accurately find out the key enzyme genes for L-lysine production in the metabolic process, and then to improve the expression of such key enzyme genes, so that the increase in L-lysine production can be achieved.

L-glutamic acid is mainly used in the production of monosodium glutamate and spices, and used as a salt substitute, nutritional supplement and biochemical reagent and so on. L-glutamic acid itself can be used as a drug to participate in the metabolism of protein and sugar in the brain, so as to promote the oxidation process. This product combines with ammonia within the body to synthesize non-toxic glutamine, which can reduce blood ammonia and alleviate the symptoms of liver coma. In the past, the production of monosodium glutamate is mainly conducted by the hydrolysis of wheat gluten (glutenin), and now, the microbial fermentation method is used for large-scale production.

SUMMARY OF INVENTION

A purpose of the present invention is to develop a new strain with the production capacity of L-amino acid, thereby to provide a method for effectively producing L-amino acid.

In order to achieve the above purpose, the inventor of the invention has found via research that NCgl0609 gene and/or NCgl1575 gene with amino acid production capacity via fermentation can have high efficient L-amino acid production capacity by modifying the gene or improving its expression, which is unknown in the prior art; in addition, the inventor of the invention also found that mutation of a certain promoter sequence can also improve the L-amino acid production capacity of corresponding microorganisms. Based on these findings, the invention is completed.

The invention provides a bacterium producing L-amino acids, wherein the expression of a polynucleotide encoding a amino acid sequence of SEQ ID NO: 3 is improved, and/or the expression of a polynucleotide encoding an amino acid sequence of SEQ ID NO: 31 is improved, and/or the bases at positions −45 bp and −47 bp of a promoter region shown in SEQ ID NO: 57 are mutated. The invention also provides a method for producing L-amino acid by using the micro-organism.

According to the invention, the improvement in expression is that the expression of the polynucleotide is enhanced or the polynucleotide encoding an amino acid sequence of SEQ ID NO: 3 or SEQ ID NO: 31 has point mutations, or the polynucleotide encoding an amino acid sequence of SEQ ID NO: 3 or SEQ ID NO: 31 has point mutations and the expression is enhanced.

A first aspect of the invention provides a bacterium that produces L-amino acid, in which the expression of poly-nucleotide encoding the amino acid sequence of SEQ ID NO: 3 is improved. Preferably, the L-amino acid is L-lysine or L-glutamic acid.

The amino acid sequence of SEQ ID NO: 3 is a protein encoded by gene NCgl0609.

The bacterium has enhanced L-amino acid production capacity.

A bacterium with L-amino acid production capacity can be a bacterium that can accumulate the target L-amino acid in the culture medium in an amount of preferably more than 0.5 g/L, more preferably more than 1.0 g/L.

The polynucleotides can encode amino acid sequences with sequence homology of about 90% or more, about 92% or more, about 95% or more, about 97% or more, about 98% or more, or about 99% or more with the amino acid sequence of SEQ ID NO: 3.

In one specific embodiment of the invention, the poly-nucleotide with improved expression contains the nucleotide sequence of SEQ ID NO: 1.

In one embodiment of the invention, the improvement in expression means that the polynucleotide encoding the amino acid sequence of SEQ ID NO: 3 has point mutations, such that arginine at position 334 of the amino acid sequence of SEQ ID NO: 3 is substituted by a terminator.

According to the invention, the amino acid sequence in which arginine at position 334 of the amino acid sequence shown in SEQ ID NO: 3 is substituted by the terminator is shown in SEQ ID NO: 4.

In one embodiment of the invention, the polynucleotide sequence with point mutation is formed by mutation of the $1000^{th}$ base of the polynucleotide sequence shown in SEQ ID NO: 1.

According to the invention, the mutation includes the mutation of the $1000^{th}$ base of the polynucleotide sequence shown in SEQ ID NO: 1 from cytosine (C) to thymine (T).

In one embodiment of the invention, the polynucleotide sequence with point mutation includes the polynucleotide sequence shown in SEQ ID NO: 2.

The invention also provides a bacterium that produces L-amino acids, which have improved expression of poly-nucleotide encoding the amino acid sequence of SEQ ID NO: 31. Preferably, the L-amino acid is L-lysine. Preferably, the bacterium is a bacterium that belongs to Corynebacte-rium genus.

The amino acid sequence of SEQ ID NO: 31 is a protein encoded by gene NCgl1575.

The microorganism has enhanced L-lysine production capacity compared with a wild type or parent strain.

The polynucleotides can encode amino acid sequences with sequence homology of about 90% or more, about 92% or more, about 95% or more, about 97% or more, about 98% or more, or about 99% or more with the amino acid sequence of SEQ ID NO: 31.

In one specific embodiment of the invention, the poly-nucleotide can contain the nucleotide sequence of SEQ ID NO: 29.

In one embodiment of the invention, the polynucleotide encoding the amino acid sequence of SEQ ID NO: 31 has point mutations, such that tyrosine at position 592 of the amino acid sequence of SEQ ID NO: 31 is substituted by different amino acids.

According to the invention, it is preferred that tyrosine at position 592 is substituted by phenylalanine.

According to the invention, the amino acid sequence in which tyrosine (Y) at position 592 of the amino acid sequence shown in SEQ ID NO: 31 is substituted by phenylalanine (F) is shown in SEQ ID NO: 32.

In one embodiment of the invention, the polynucleotide sequence with point mutation is formed by mutation of the $1775^{th}$ base of the polynucleotide sequence shown in SEQ ID NO: 29.

According to the invention, the mutation includes the mutation of the $1775^{th}$ base of the polynucleotide sequence shown in SEQ ID NO: 29 from adenine (A) to thymine (T).

In one embodiment of the invention, the polynucleotide sequence with point mutation includes the polynucleotide sequence shown in SEQ ID NO: 30.

According to the invention, the bacterium can be a microorganism that belongs to Corynebacterium genus, such as Corynebacterium glutamicum, Brevibacterium fla-vum, Brevibacterium lactofermentum, Corynebacterium ammoniagenes, Corynebacterium pekinense.

In one embodiment of the invention, the microorganism belonging to Corynebacterium genus is Corynebacterium glutamicum YP97158, with the deposition number CGMCC No. 12856, deposited on Aug. 16, 2016, the depository unit is the General Microbiology Center of China Microbial Species Conservation and Management Commission, No. 3, Yard. 1 Beichen West Road, Chaoyang District, Beijing, Tel: 010-64807355, recorded in Chinese patent application CN106367432A (the filing date: Sep. 1, 2016, publication date: Feb. 1, 2017).

In one embodiment of the invention, the microorganism belonging to Corynebacterium genus is Corynebacterium glutamicum ATCC 13869.

The expression of polynucleotides can be enhanced by the following means: substitution or mutation in expression regulation sequences, introduction of mutation to polynucle-otide sequences, increase of the number of copies of poly-nucleotides introduced through chromosome insertion or vector, or combinations thereof.

The expression regulation sequences of polynucleotides can be modified. The expression regulation sequences con-trol the expression of polynucleotides to which they are operably linked, and may include promoters, terminators, enhancers, silencers, and the like, for example. Polynucle-otides can have changes in the starting codon. Polynucle-otides can be incorporated into specific sites of chromo-somes so as to increase the number of copies. Herein, specific sites may include, for example, transposon sites or intergenic sites. In addition, polynucleotides can be incor-porated into an expression vector, and the expression vector can be introduced into host cells to increase the number of copies.

In one embodiment of the invention, the number of copies is increased by incorporating polynucleotides or polynucle-otides with point mutations to specific sites of microbial chromosomes.

In one embodiment of the invention, the nucleic acid sequence is overexpressed by incorporating polynucleotides with promoter sequences or polynucleotides with promoter sequences and point mutations into specific sites of microbial chromosomes.

In one embodiment of the invention, the number of copies is increased by incorporating polynucleotides or polynucleotides with point mutations into expression vectors, and introducing the expression vectors into host cells.

In one embodiment of the invention, the amino acid sequence is overexpressed by incorporating polynucleotides with promoter sequences or the polynucleotides with promoter sequences and point mutations into expression vectors, and introducing the expression vectors into host cells.

In one specific embodiment of the invention, the promoter is the promoter of polynucleotide (NCgl0609 gene) encoding the amino acid sequence of SEQ ID NO: 3.

In one specific embodiment of the invention, the promoter is the promoter of polynucleotide (NCgl1575 gene) encoding the amino acid sequence of SEQ ID NO: 31.

In some specific embodiments of the invention, the vectors used are pK18mobsacB plasmid and pXMJ19 plasmid.

According to the invention, the bacterium can also have other improvements associated with increase in the production of L-amino acids.

The second aspect of the invention provides a polynucleotide sequence, an amino acid sequence encoded by the polynucleotide sequence, a recombinant vector including the polynucleotide sequence, and a recombinant strain containing the polynucleotide sequence.

According to the invention, the polynucleotide sequence has improved expression, and the improvement includes point mutations of polynucleotide encoding polypeptide containing amino acid sequence shown in SEQ ID NO: 3, such that arginine at 334 position of the amino acid sequence is substituted by a terminator.

According to the invention, the amino acid sequence in which arginine at 334 position of the amino acid sequence shown in SEQ ID NO: 3 is substituted by a terminator is shown in SEQ ID NO: 4.

According to the invention, the polynucleotide sequence encoding the polypeptide containing the amino acid sequence shown in SEQ ID NO: 3 contains the polynucleotide sequence shown in SEQ ID NO: 1.

In one embodiment of the invention, the mutated polynucleotide sequence provided by the invention is formed by mutation of the $1000^{th}$ base of the polynucleotide sequence shown in SEQ ID NO: 1.

According to the invention, the mutation includes the mutation of the $1000^{th}$ base of the polynucleotide sequence shown in SEQ ID NO: 1 from cytosine (C) to thymine (T).

In one embodiment of the invention, the mutated polynucleotide sequence includes the polynucleotide sequence shown in SEQ ID NO: 2.

According to the invention, the substituted amino acid sequence includes the amino acid sequence shown in SEQ ID NO: 4.

According to the invention, the polynucleotide sequence includes polynucleotide encoding polypeptides containing amino acid sequence shown in SEQ ID NO: 31, wherein tyrosine at position 592 is substituted by different amino acids.

According to the invention, preferably, tyrosine at position 592 is substituted by phenylalanine.

According to the invention, the amino acid sequence in which tyrosine (Y) at position 592 of the amino acid sequence shown in SEQ ID NO: 31 is substituted by phenylalanine (F) is shown in SEQ ID NO: 32.

According to the invention, preferably, the polynucleotide sequence encoding the polypeptide containing the amino acid sequence shown in SEQ ID NO: 31 contains the polynucleotide sequence shown in SEQ ID NO: 29.

In one embodiment of the invention, the polynucleotide sequence is formed by mutation of the 1775th base of the polynucleotide sequence shown in SEQ ID NO: 29.

According to the invention, the mutation includes the mutation of the $1775^{th}$ base of the polynucleotide sequence shown in SEQ ID NO: 29 from adenine (A) to thymine (T).

In one embodiment of the invention, the polynucleotide sequence includes the polynucleotide sequence shown in SEQ ID NO: 30.

According to the invention, the amino acid sequence includes the amino acid sequence shown in SEQ ID NO: 32.

According to the invention, the mutation refers to change of the base/nucleotide of the site. The mutation method can be selected from at least one of mutagenesis, PCR site directed mutation method, and/or homologous recombination method. In the invention, PCR site directed mutation method and/or homologous recombination method are preferred.

According to the invention, the recombinant vector is constructed by introducing the polynucleotide sequence into the plasmid.

In one embodiment of the invention, the plasmid is pK18mobsacB plasmid.

In another embodiment of the invention, the plasmid is pXMJ19 plasmid.

Specifically, the polynucleotide sequence and the plasmid can be constructed into a recombinant vector via a NEBuider recombination system.

According to the invention, the recombinant strain contains the polynucleotide sequence.

As one embodiment of the invention, the starting strain of the recombinant strain is YP97158.

As one embodiment of the invention, the starting strain of the recombinant strain is ATCC 13869.

The third aspect of the invention also provides a method for constructing a recombinant strain for producing L-amino acid.

According to the invention, the construction method includes the following steps:

Modifying the polynucleotide sequence of wild-type NCgl0609 shown in SEQ ID NO: 1 in a host strain to mutate its $1000^{th}$ base, so as to obtain a recombinant strain containing the mutated NCgl0609 encoding gene.

According to the construction method of the invention, the modification includes at least one of mutagenesis, PCR site directed mutation method, and/or homologous recombination method.

According to the construction method of the invention, the mutation refers to the mutation of the 1000th base in SEQ ID NO: 1 from cytosine (C) to thymine (T); Specifically, the polynucleotide sequence containing the mutated NCgl0609 encoding gene is shown in SEQ ID NO: 2.

Further, the construction method comprises the following steps:

(1) Modifying the nucleotide sequence of wild-type NCgl0609 gene as shown in SEQ ID NO: 1 to mutate its 1000th base, so as to obtain the mutated polynucleotide sequence of NCgl0609 gene;

(2) Linking the mutated polynucleic acid sequence with a plasmid to construct a recombinant vector; and (3) Introducing the recombinant vector into a host strain to obtain the recombinant strain containing the mutated NCgl0609 encoding gene.

According to the construction method of the invention, the step (1) includes: constructing the NCgl0609 gene with point mutation: synthesizing two pairs of primers P1 and P2, P3 and P4 for amplifying NCgl0609 gene fragments based on the genome sequence of the unmodified strain, and introducing point mutation into SEQ ID NO: 1 of wild-type NCgl0609 gene by PCR site directed mutation method, to obtain the nucleotide sequence SEQ ID NO: 2 of NCgl0609 gene with point mutation, which is recorded as NCgl0609$^{C1000T}$.

In one embodiment of the invention, the genome of the unmodified strain can be derived from ATCC13032 strain, and its genome sequence can be obtained from NCBI website.

In one embodiment of the invention, in the step (1), the primers are:

```
P1:
                              (SEQ ID NO: 5)
5'CAGTGCCAAGCTTGCATGCCTGCAGGTCGACTCTAGG

GACGGCAACGTACATAAC3',

P2:
                              (SEQ ID NO: 6)
5' GTTGCCGGTGAGTCAAACAGTCATTTTGC 3',

P3:
                              (SEQ ID NO: 7)
5' GCAAAATGACTGTTTGACTCACCGGCAAC 3',
and P4:
                              (SEQ ID NO: 8)
5' CAGCTATGACCATGATTACGAATTCGAGCTCGGTACC

CGCGGCTG GAAATGTGGAG3'.
```

In one embodiment of the invention, the PCR amplification is carried out as follows: pre-denaturation for 5 min at 94° C., denaturation for 30 s at 94° C., annealing for 30 s at 52° C., extension for 40 s at 72° C. (30 cycles), and over extension for 10 min at 72° C.

In one embodiment of the invention, the overlap PCR amplification is carried out as follows: pre-denaturation for 5 min at 94° C., denaturation for 30 s at 94° C., annealing for 30 s at 52° C., extension for 60 s at 72° C. (30 cycles), and over extension for 10 min at 72° C.

According to the construction method of the invention, the step (2) includes the construction of a recombinant plasmid, including: assembling the separated and purified NCgl0609$^{C1000T}$ and pK18mobsacB plasmids through a NEBuider recombination system to obtain the recombinant plasmid.

According to the construction method of the invention, the step (3) includes construction of a recombinant strain: transforming the recombinant plasmid into a host strain, to obtain the recombinant strain.

In one embodiment of the invention, the transforming in the step (3) is an electric transforming method.

In one embodiment of the invention, the host strain is YP97158.

In one embodiment of the invention, the recombination is achieved by homologous recombination.

The fourth aspect of the invention also provides a method for constructing a recombinant strain for producing L-amino acid.

According to the invention, the construction method includes the following steps:

Amplifying the upstream and downstream homologous arm fragments of NCgl0609 gene, the coding region of NCgl0609 gene and its promoter region sequence, or amplifying the coding region of NCgl0609 or NCgl0609$^{R334*}$ gene and its promoter region sequence, and then introducing NCgl0609 or NCgl0609$^{R334*}$ gene into the genome of a host strain by homologous recombination, so as to obtain the overexpression of NCgl0609 or NCgl0609$^{R334*}$ gene in the strain.

In one embodiment of the invention, the primers for amplifying the upstream homologous arm fragment are:

```
P7:
                              (SEQ ID NO: 11)
5'CAGTGCCAAGCTTGCATGCCTGCAGGTCGACTCTAG

AATGCGTTCTG GACTGAGG

3',
and
P8:
                              (SEQ ID NO: 12)
5' GAGATGATCCTCGCAGCTGGTGCACCGAGAACAGATG 3'.
```

In one embodiment of the invention, the primers for amplifying the downstream homologous arm fragment are:

```
P11:
                              (SEQ ID NO: 15)
5' GGTCAAGGAAGGAGTTGTTGCCAGAATCAGATG

GCGCAATTA AATC AAG 3',
and

P12:
                              (SEQ ID NO: 16)
5' CAGCTATGACCATGATTACGAATTCGAGCTCGGTA

CCCGCTATGACACCTTCAACGGATC 3'.
```

In one embodiment of the invention, the primers for amplifying the sequence of the gene coding region and its promoter region are:

```
P9:
                              (SEQ ID NO: 13)
5' CATCTGTTCTCGGTGCACCAGCTGCGAGGATCATCTC 3',
and P10:
                              (SEQ ID NO: 14)
5' GATTTAATTGCGCCATCTGATTCTGGCAACAACTCC

TTCCTTGACC 3'.
```

In one embodiment of the invention, the above P7-P12 are used as primers, and the upstream homologous fragment, downstream homologous fragment and NCgl0609 or NCgl0609$^{R334*}$ fragment with its own promoter obtained through amplification are mixed as templates for amplification, so as to obtain an integrated homologous arm fragment.

In one embodiment of the invention, PCR system used is: 10×Ex Taq Buffer 5 μL, dNTP Mixture (each 2.5 mM) 4 μL, Mg$^{2+}$ (25 mM) 4 μL, primers (10 pM) each 2 μL, Ex Taq (5 U/μL) 0.25 μL, total volume: 50 μL; the PCR amplification is carried out as follows: pre-denaturation for 5 min at 94° C., denaturation for 30 s at 94° C., annealing for 30 s at 52° C., extension for 60 s at 72° C. (30 cycles), and over extension for 10 min at 72° C.

In one embodiment of the invention, a shuttle plasmid PK18mobsacB is assembled with upper and lower homologous arm fragments, gene coding region and promoter region fragments, by using a NEBuider recombination system, so as to obtain the integrated plasmid.

In one embodiment of the invention, the integrated plasmid is transfected into the host strain, and NCgl0609 or NCgl0609$^{R334*}$ gene is introduced into the genome of the host strain by homologous recombination.

In one embodiment of the invention, the host strain is YP97158.

In one embodiment of the invention, the host strain is a strain carrying the polynucleotide sequence shown in SEQ ID NO: 2.

The fifth aspect of the invention also provides a method for constructing a recombinant strain for producing L-amino acid.

According to the invention, the construction method includes the following steps:

Amplifying the NCgl0609 gene coding region and promoter region sequence, or the NCgl0609$^{R334*}$ gene coding region and promoter region sequence, constructing an overexpression plasmid vector, and transferring the vector into a host strain to achieve overexpression of NCgl0609 or NCgl0609$^{R334*}$ in the strain.

In one embodiment of the invention, the primers for amplifying the sequence of the gene coding region and its promoter region are:

```
P17:
                                  (SEQ ID NO: 21)
5'GCTTGCATGCCTGCAGGTCGACTCTAGAGGATCCCCCAGC

TGCGAGG A TCATCTC3',
and
P18:
                                  (SEQ ID NO: 22)
5'ATCAGGCTGAAAATCTTCTCTCATCCGCCAAAACCAACA

ACTCCTTCCTTGACC3'.
```

In one embodiment of the invention, the PCR system is: 10×Ex Taq Buffer 5 μL, dNTP Mixture (each 2.5 mM) 4 μL, Mg$^{2+}$ (25 mM) 4 μL, primer (10 μM) each 2 μL, Ex Taq (5 U/μL) 0.25 μL, total volume 50 μL; the PCR amplification is carried out as follows: pre-denaturation for 5 min at 94° C., denaturation for 30 s at 94° C., annealing for 30 s at 52° C., extension for 60 s at 72° C. (30 cycles), and over extension for 10 min at 72° C.

In one embodiment of the invention, a shuttle plasmid pXMJ19 is assembled with NCgl0609 and NCgl0609$^{R334*}$ fragments with their own promoters by using a NEBuider recombination system, so as to obtain the overexpression plasmid.

In one embodiment of the invention, the host strain is YP97158.

In one embodiment of the invention, the host strain is ATCC 13869.

In one embodiment of the invention, the host strain is a strain carrying the polynucleotide sequence shown in SEQ ID NO: 2.

The invention also provides a method for constructing a corynebacterium recombinant strain.

According to the invention, the construction method includes the following steps:

Modifying the polynucleotide sequence of wild-type NCgl1575 in the host strain as shown in SEQ ID NO:

29 to mutate its 1775$^{th}$ base, so as to obtain a Corynebacterium recombinant strain containing the mutated NCgl1575 encoding gene.

According to the construction method of the invention, the modification includes at least one of mutagenesis, PCR site directed mutation method, and/or homologous recombination.

According to the construction method of the invention, the mutation refers to the mutation of the 1775th base in SEQ ID NO: 29 from adenine (A) to thymine (T); Specifically, the polynucleotide sequence containing the mutated NCgl1575 encoding gene is shown in SEQ ID NO: 30.

Further, the construction method comprises the following steps:

(1) Modifying the nucleotide sequence of wild-type NCgl1575 gene shown in SEQ ID NO: 29 to mutate its 1775th base, so as to obtain the mutated polynucleotide sequence of NCgl1575 gene;

(2) Linking the mutated polynucleic acid sequence with a plasmid to construct a recombinant vector; and (3) Introducing the recombinant vector into a host strain to obtain the Corynebacterium recombinant strain containing the mutated NCgl1575 encoding gene.

According to the construction method of the invention, the step (1) includes: constructing the NCgl1575 gene with point mutation: synthesizing two pairs of primers P1' and P2', and P3' and P4' for amplifying NCgl1575 gene fragments, based on the genome sequence of Corynebacterium glutamicum, and introducing point mutation into SEQ ID NO: 29 of wild-type NCgl1575 gene by PCR site directed mutation method, to obtain the nucleotide sequence SEQ ID NO: 30 of NCgl1575 gene with point mutation, which is recorded as NCgl1575$^{A1775T}$.

In one embodiment of the invention, the genome of Corynebacterium glutamicum can be derived from ATCC13032 strain, and its genome sequence can be obtained from NCBI website.

In one embodiment of the invention, in the step (1), the primers are:

```
P1':
                                  (SEQ ID NO: 33)
5'CAGTGCCAAGCTTGCATGCCTGCAGGTCGACTCTAGTGCGTT

CGTCTGCGGTTTCG 3';
P2':
                                  (SEQ ID NO: 34)
5' ATCGACGCCGCCCCATTCACCCTTCTGATG 3';
P3':
                                  (SEQ ID NO: 35)
5' CATCAGAAGGGTGAATGGGCGGCGTCGAT 3';
and P4':
                                  (SEQ ID NO: 36)
5'CAGCTATGACCATGATTACGAATTCGAGCTCGGTACCC

AAGCCTCGACCCCTACATC 3'.
```

In one embodiment of the invention, the PCR amplification is carried out as follows: denaturation for 30 s at 94° C., annealing for 30 s at 52° C., and extension for 40 s at 72° C. (30 cycles).

In one embodiment of the invention, the overlap PCR amplification is carried out as follows: denaturation for 30 s at 94° C., annealing for 30 s at 52° C., and extension for 90 s at 72° C. (30 cycles).

According to the construction method of the invention, the step (2) includes the construction of a recombinant plasmid, including: assembling the separated and purified NCgl1575$^{A1775T}$ and pK18mobsacB plasmids through a NEBuider recombination system to obtain the recombinant plasmid pK18-NCgl1575$^{A1775T}$.

According to the construction method of the invention, the step (3) includes construction of a recombinant strain: transforming the recombinant plasmid pK18-NCgl1575$^{A1775T}$ into a host strain, to obtain the recombinant strain.

In one embodiment of the invention, the transforming in the step (3) is an electric transforming method.

In one embodiment of the invention, the host strain is YP97158.

In one embodiment of the invention, the recombination is achieved by homologous recombination.

The invention also provides a method for constructing a *corynebacterium* recombinant strain.

According to the invention, the construction method includes the following steps:

Amplifying the upstream and downstream homologous arm fragments of NCgl1575 gene, the coding region of NCgl1575 gene and its promoter region sequence, or the coding region of NCgl1575$^{A1775T}$ gene and its promoter region sequence, and introducing NCgl1575 or NCgl1575$^{A1775T}$ gene into the genome of a host strain by homologous recombination, so as to achieve overexpression of NCgl1575 or NCgl1575$^{A1775T}$ gene in the strain.

In one embodiment of the invention, the primers for amplifying the upstream homologous arm fragment are:

```
P7':
                                 (SEQ ID NO: 39)
5' CAGTGCCAAGCTTGCATGCCTGCAGGTCGACTCTAGAATG

CGTTCTGGACTGAGG 3';
and

P8':
                                 (SEQ ID NO: 40)
5' GAAACGGCCTTAAGCTAGGTGCACCGAG AACAGATG 3'.
```

In one embodiment of the invention, the primers for amplifying the downstream homologous arm fragment are:

```
P11':
                                 (SEQ ID NO: 43)
5' AACCGGGCGG GAAAAGCTTGATGGCGCAATTAAATCAAG 3';
and P12':
                                 (SEQ ID NO: 44)
5'CAGCTATGACCATGATTACGAATTCGAGCTCGGTACCC GCTAT

GACACCTTCAACGGATC 3'.
```

In one embodiment of the invention, the primers for amplifying the sequence of the gene coding region and its promoter region are:

```
P9':
                                 (SEQ ID NO: 41)
5' CATCTGTTCTCGGTGCAC CTAGCTTAAG GCCGTTTC 3';
and P10':
                                 (SEQ ID NO: 42)
5' CTTGATTTAATTGCGCCATCAAGCTTTTCC CGCCCGGTT 3'.
```

In one embodiment of the invention, the above P7'/P12' are used as primers, and the upstream homologous fragment, downstream homologous fragment and NCgl1575 or NCgl1575$^{A1775T}$ fragment with its own promoter obtained through amplification are mixed as templates for amplification, so as to obtain an integrated homologous arm fragment.

In one embodiment of the invention, PCR system used is: 10×Ex Taq Buffer 5 μL, dNTP Mixture (each 2.5 mM) 4 μL, Mg$^{2+}$ (25 mM) 4 μL, primers (10 pM) each 2 μL, Ex Taq(5 U/μL) 0.25 μL, total volume 50 μL; PCR amplification is carried out as follows: pre-denaturation for 5 min at 94° C., denaturation for 30 s at 94° C., annealing for 30 s at 52° C., extension for 180 s at 72° C. (30 cycles), and over extension for 10 min at 72° C.

In one embodiment of the invention, a shuttle plasmid PK18mobsacB is assembled with the intergrated homologous arm fragment, by using a NEBuider recombination system, so as to obtain the integrated plasmid.

In one embodiment of the invention, the integrated plasmid is transfected into the host strain, and NCgl1575 or NCgl1575$^{A1775T}$ gene is introduced into the genome of the host strain by homologous recombination.

In one embodiment of the invention, the host strain is YP97158.

In one embodiment of the invention, the host strain is a strain carrying the polynucleotide sequence shown in SEQ ID NO: 30.

The invention also provides a method for constructing a *Corynebacterium* recombinant strain.

According to the invention, the construction method includes the following steps:

Amplifying the NCgl1575 gene coding region and promoter region sequence, or the NCgl1575$^{A1775T}$ gene coding region and promoter region sequence, constructing an overexpression plasmid vector, and transferring the vector into a host strain to achieve overexpression of NCgl1575 or NCgl1575$^{A1775T}$ gene in the strain.

In one embodiment of the invention, the primers for amplifying the sequence of the gene coding region and its promoter region are:

```
P17':
                                 (SEQ ID NO: 49)
5'GCTTGCATGCCTGCAGGTCGACTCTAGAGGATCCCC CTAGCT

TAAG GCCGTTTC 3';
and

P18':
                                 (SEQ ID NO: 50)
5'ATCAGGCTGAAAATCTTCTCTCATCCGCCAAAAC AAGCTTT

TCC CGCCCGGTT 3'.
```

In one embodiment of the invention, the PCR system is: 10×Ex Taq Buffer 5 μL, dNTP Mixture (each 2.5 mM) 4 μL, Mg$^{2+}$ (25 mM) 4 μL, primers (10 pM) each 2 μL, Ex Taq(5 U/μL) 0.25 μL, total volume 50 μL; the PCR amplification is carried out as follows: pre-denaturation for 5 min at 94° C., denaturation for 30 s at 94° C., annealing for 30 s at 52° C., extension for 120 s at 72° C. (30 cycles), and over extension for 10 min at 72° C.

In one embodiment of the invention, a shuttle plasmid pXMJ19 is assembled with NCgl1575 or NCgl1575$^{A1775T}$ fragments with their own promoters by using a NEBuider recombination system, so as to obtain the overexpression plasmid.

In one embodiment of the invention, the host strain is YP97158.

In one embodiment of the invention, the host strain is a strain carrying the polynucleotide sequence shown in SEQ ID NO: 30.

Another aspect of the invention is to provide a promoter nucleotide sequence, which includes the nucleotide sequence formed by mutation of bases at positions −45 bp and −47 bp in the promoter region shown in SEQ ID NO: 57.

According to the invention, nucleotide guanine (G) at position −45 bp is mutated to adenine (A), and nucleotide guanine (G) at position −47 bp is mutated to thymine (T) in the promoter region shown in SEQ ID NO: 57.

According to the invention, the promoter nucleotide sequence is as follows:

(a) the nucleotide sequence shown in SEQ ID NO: 58; or, (b) the nucleotide sequence having a sequence identity of more than 90%, preferably more than 95%, 98% to nucleotide sequence shown in SEQ ID NO: 58, and retaining enhanced activity of the promoter of (a), with at position −45 bp remaining as adenine (A), and at position −47 bp remaining as thymine (T).

The invention also provides an expression cassette containing the above promoter, including the promoter and an encoding sequence that can be operatively connected behind the promoter. In one embodiment of the invention, the encoding sequence is the encoding sequence of lysC gene.

The invention also provides a recombinant vector containing the promoter nucleotide sequence of the invention.

According to the invention, the recombinant vector is constructed by linking the promoter nucleotide sequence of the invention with a shuttle plasmid; as an embodiment of the invention, the shuttle plasmid is pK18mobsacB plasmid.

The invention also provides a recombinant strain comprising the promoter nucleotide sequence or the recombinant vector above.

The recombinant strain according to the invention comprises the nucleotide sequence shown in SEQ ID NO: 58. The nucleotide sequence shown in SEQ ID NO: 58 is the promoter region of lysC gene. Further, the nucleotide sequence shown in SEQ ID NO: 58 is linked with the lysC gene encoding sequence. In particular, the recombinant strain can include expression the cassette or the recombinant vector as described above in the invention. In particular, the recombinant strain of the invention is obtained by transforming the expression cassette or the recombinant vector. The recombinant strain according to the invention is formed by introducing the nucleotide sequence of the mutated promoter above into a host strain for recombination; the host strain can be selected from strains that produce L-amino acid, especially L-lysine, as known in the art, for example, at least one selected from *Corynebacterium*. The *Corynebacterium* can be *Corynebacterium glutamicum, Corynebacterium flavum, Corynebacterium crenatum* and *Corynebacterium pekinene; Corynebacterium glutamicum* is preferred. As an embodiment of the invention, the host strain is YP97158.

The recombinant strain according to the invention uses the pK18mobsacB plasmid as the vector.

The recombinant strain according to the invention may further include other modifications.

The invention also provides a method for constructing a recombinant strain producing L-lysine, which comprises the following step:

(1) Modifying the promoter region shown in SEQ ID NO:57, to mutate position −45 bp and −47 bp, so as to obtain the nucleotide sequence containing the mutated promoter region.

According to the invention, the mutation refers to the mutation of nucleotide guanine (g) at position −45 bp to adenine (a) and nucleotide guanine (g) at position −47 bp to thymine (T) in the promoter region shown in SEQ ID NO: 57. Specifically, the nucleotide sequence of the mutated promoter region is shown in SEQ ID NO: 58. Further, the construction method further comprises the following steps:

(2) Linking the nucleotide sequence of the mutated promoter region with a plasmid to construct a recombinant vector; and (3) Introducing the recombinant vector into a host strain to obtain the recombinant strain producing L-lysine containing the mutated promoter region.

According to the invention, the method of mutation in step (1) includes mutagenesis, PCR site directed mutation or homologous recombination, preferably PCR site directed mutation.

According to the invention, the step (1) comprises:

Designing two pairs of primers to amplify the promoter region of lysc gene, and then obtaining the nucleotide sequence of the mutated promoter region by PCR technology.

In an embodiment of the present invention, the primers in step (1) are:

```
P1":
                                  (SEQ ID NO: 59)
5' CCGGAATTCG ACCAAGGATG AGGGCTTTG 3';
(EcoR I)

P2":
                                  (SEQ ID NO: 60)
5' AGTTACCCGC TCAATTATAC CTTTATAAAC 3';

P3":
                                  (SEQ ID NO: 61)
5' GTTTATAAAG GTATAATTGA GCGGGTAACT 3';
and P4":
                                  (SEQ ID NO: 62)
5' ACATGCATGC GCGTACGCGA AGTGGCACAT 3'.
(Sph I)
```

In one embodiment of the present invention, the step (1) includes: using *Corynebacterium glutamicum* ATCC13032 as a template and using primers P1" and P2", P3" and P4", respectively, to perform PCR amplification to obtain two DNA fragments; Using the above two DNA fragments as templates and P1" and P4" as primers, to obtain the DNA fragment containing the promoter region nucleotide sequence (SEQ ID NO: 58) of the present invention by overlap PCR amplification.

According to the invention, in step (1), the DNA fragment obtained through overlap PCR amplification contains EcoR I and Sph I enzyme digestion sites at both ends, respectively.

According to the invention, the step (2) includes: subjecting the product amplified through overlap PCR reaction to agarose gel electrophoresis and separation and purification, connecting the fragment via double enzyme digestion (EcoR I/Sph I) with a shuttle plasmid avia the same double enzyme digestion ((EcoR I/Sph I)), to obtain an allelic replaced recombinant vector.

According to the invention, the shuttle plasmid is a pK18mobsacB plasmid; and the constructed recombinant vector is pK18-Plys C$^{(G(-45)A,G(-47)T)}$.

In one embodiment of the present invention, the recombinant plasmid has a kanamycin resistance marker.

In one embodiment of the present invention, the transformation of step (3) is an electric transformation method;

exemplary, in step (3), the recombinant vector is transformed into the strain YP97158.

The above various recombinant strains obtained by the invention can be used in fermentation to produce L-amino acids alone or in combination, or can be mixed with other bacterium producing L-amino acids for fermentation, so as to produce L-amino acids.

Another aspect of the invention provides a method for producing L-amino acids, which includes culturing the bacterium; and obtaining L-amino acids from the culture.

The bacterium can be cultured in a suitable medium under culture conditions known in the art. The culture medium can contain a carbon source, a nitrogen source, trace elements, and their combinations. In culture, the pH of the culture can be adjusted. In addition, in culture, the prevention of bubble generation can be included, for example, by using defoamers to prevent bubble from generating. In addition, in culture, the injection of gas into the culture can be included. Gases may include any gas capable of maintaining the aerobic conditions of the culture. In culture, the temperature of the culture can be 20 to 45° C. The generated L-amino acids can be recovered from the culture, that is, the culture is treated with sulfuric acid or hydrochloric acid, etc., followed by a combination of methods such as anion exchange chromatography, concentration, crystallization, and isoelectric point precipitation.

In the invention:

```
SEQ ID NO: 1: NCgl0609 wild-type ORF sequence:
GTGTCACACACCGCGTCCACACCGACGCCAGAGGAATACTCCGC

GCAGCAACCCAGCACCCAGGGCACTCGCGTTGAGTTCCGCGGCA

TAACCAAAGTCTTTAGCAACAATAAATC TGCTAAAACCACCGC

GCTTGATAATGTCACTCTCACCGTAGAACCCGGTGAGGTAATCG

GCATCATCGGTTACTCTGGCGCCGGCAAGTCCACTCTTGTCCGC

C TCATCAATGGCCTTGACTCCCCCACGAGCGGTTCGTTGCTGC

TCAACGGCACCGACATCGTCGGAATGCCCGAGTCTAAGCTGCGT

AAACTGCGCAGTAATATCGGCATGATTTTCCAGCAGTTCAACCT

GTTCCAGTCGCGTACTGCGGCTGGAAATGTGGAGTACCCGCTGG

AAGTTGCCAAGATGGACAAGGCAGCTCGTAAAGCTCGCGTGCAA

GAAATGCTCGAGTTCGTCGGCCTGGG CGACAAAGGCAAAAACT

ACCCCGAGCAGCTGTCGGGCGGCCAGAAGCAGCGCGTCGGCATT

GCCCGTGCACTGGCCACCAATCCAACGCTTTTGCTTGCCGACGA

AGCCACCTCCGCTTTGGACCCAGAAACCACCCATGAAGTTCTGG

AGCTGCTGCGCAAGGTAAACCGCG AACTGGGCATCACCATCGT

TGTGATCACCCACGAAATGGAAGTTGTGCGTTCCATCGCAGACA

AGGTTGCTGTGATGGAATCCGGCAAAGTTGTGGAATACGGCAGC

GTCTACGAGGTGTTCT CCAATCCACA AACACAGGTTGCTCAA

AAGT TCGTGGCCAC CGCGCTGCGT AACACCCCAGACCAAGT

GGAATCGGAAGATCTGCTTAGCCATGAGGGACGTCTGTTCACCA

TTGATCTGACTGAAACGTCCGGCTTCTTTGCAGCAACCGCTCGT

GCTGCCGAACAA GGTGCTTTTGTCAACATCGTTCACGGTGGCG

TGACCACCTTGCAACGCCAATCATTTGG CAAAATGACTGTTCG
```

-continued

```
ACTCACCGGCAACACCGCTGCGATTGAAGAGTTCTATCAAACC

TTGACC AAGACCACGA CCATCAAGGA GATCACCCGATGA

SEQ ID NO: 2: NCgl0609^{R334*} ORF sequence:
GTGTCACACA CCGCGTCCAC ACCGACGCCA GAGGAATACT

CCGCGCAGCAACCCAGCACCCAGGGCACTCGCGTTGAGTTCCGC

GGCATAACCAAAGTCTTTAGCAACAATAAATCTGCTAAAACCAC

CGCGCTTGATAATGTCACTCTCACCGTAGAACCCGGTGAGGTAA

TCGGCATCATCGGTTACTCTGGCGCCGGCAAGTCCACTCTTGTC

CGCCTCATCAATGGCCTTGACTCCCCCACGAGCGGTTCGTTGCT

GCTCAACGGCACCGACATCGTCGGAATGCCCGAGTCTAAGCTGC

GTAAACTGCGCAGTAATATCGGCATGATTTTCCAGCAGTTCAAC

CTGTTCCAGTCGCGTACTGCGGCTGGAAATGTGGAGTACCCGCT

GGAAGTTGCCAAGATGGACAAGGCAGCTCGTAAAGCTCGCGTGC

AAGAAATGCTCGAGTTCGTCGGCCTGGGCGACAAAGGCAAAAAC

TACCCCGAGCAGCTGTCGGGCGGCCAGAAGCAGCGCGTCGGCAT

TGCCCGTGCACTGGCCACCAATCCAACGCTTTTGCTTGCCGACG

AAGCCACCTCCGCTTTGGACCCAGAAACCACCCATGAAGTTCTG

GAGCTGCTGCGCAAGGTAAACCGCGAACTGGGCATCACCATCGT

TGTGATCACCCACGAAATGGAAGTTGTGCGTTCCATCGCAGACA

AGGTTGCTGTGATGGAATCCGGCAAAGTTGTGGAATACGGCAGC

GTCTACGAGGTGTTCTCCAATCCACAAACACAGGTTGCTCAAAA

GTTCGTGGCCACCGCGCTGCGTAACACCCCAGACCAAGTGGAAT

CGGAAGATCTGCTTAGCCATGAGGGACGTCTGTTCACCATTGAT

CTGACTGAAACGTCCGGCTTCTTTGCAGCAACCGCTCGTGCTGC

CGAACAAGGTGCTTTTGTCAACATCGTTCACGGTGGCGTGACCA

CCTTGCAACGCCAATCATTTGGCAAAATGACTGTTTGACTCACC

GGCAACACCGCTGCGATTGAAGAGTTCTATCAAACCTTGACC A

AGACCACGA CCATCAAGGA GATCACCCGATGA

SEQ ID NO: 3: NCgl0609 wild-type coding
protein amino acid sequence:
MSHTASTPTPEEYSAQQPSTQGTRVEFRGITKVFSNNKSAKTTA

LDNVTLTVEPGEVIGIIGYSGAGKSTLVRLINGLDSPTSGSLLL

NGTDIVGMPESKLRKLRSNIGMIFQQFNLFQSRTAAGNVEYPLE

VAKMDKAARKARVQEMLEFVGLGDKGKNYPEQLSGGQKQRVGIA

RALATNPTLLLADEATSALDPETTHEVLELLRKVNRELGITIVV

ITHEMEVVRSIADKVAVMESGKVVEYGSVYEVFSNPQTQVAQKF

VATALRNTPDQVESEDLLSHEGRLFTIDLTETSGFFAATARAAE

QG AFVNIVHGGV TTLQRQSFGK MTVRLTGNTA AIEEFYQT

LT KTTTIKEITR

SEQ ID NO: 4: NCgl0609R334* coding protein
amino acid sequence:
MSHTASTPTPEEYSAQQPSTQGTRVEFRGITKVFSNNKSAKTTA

LDNVTLTVEPGEVIGIIGYSGAGKSTLVRLINGLDSPTSGSLLL
```

-continued

NGTDIVGMPESKLRKLRSNIGMIFQQFNLFQSRTAAGNVEYPLE

VAKMDKAARKARVQEMLEFVGLGDKGKNYPEQLSGGQKQRVGIA

RALATNPTLLLADEATSALDPETTHEVLELLRKVNRELGITIVV

ITHEMEVVRSIADKVAVMESGKVVEYGSVYEVFSNPQTQVAQKF

VATALRNTPDQVESEDLLSHEGRLFTIDLTETSGFFAATARAAE

QG AFVNIVHGGV TTLQRQSFGK MTV

SEQ ID NO: 29: NCgl1575 wild-type ORF sequence:
ATGGCAGAATCAAACGCTATGGACCGGGCACAAATCTCTGCACT

GCTAGATAGAGCACAGCACACAATCAACCTTGCCGAACAAGCAA

ACAACGTGCTCCGACTGTTGAAAACACCCGGAACGGCCACAGTA

GGGGACAACGGGACACTCGGCACCGATACCTATCTGATCCCATC

CCGCAACATCACCTGGCCTGACAACCTGTATGTCAACGTCTTTC

TAGACGGCATGAATGCAGAAGCCACCCTTACCGATTACGTCGCA

TCAGTCGCTTCGATCCCACGCCTATGCCAGATCATCAACGAGGG

CCAAGGCGGCATGTTCCGCAGACTATTCAACCCCACCAAGGTCC

AAGCCGGCGACCAAGCTGTCTTCGACCTCATGGTCAAACTCGAC

GAGATTTCATCTACCACCCACGAAGTCTCCCGCATGCTCGAGGG

CGTCCACGCTGCCCGCACCCGCCAACAACAAGGCGTTGCACTTT

TCCCAGGTATTCATGGAGTGGGAGAGCGCTACATCGAACGCGCA

CAACAGGTACTCGCCTCAGCCCTCGGTATCGCTGGATTCGGTGC

CGAACCCTGGGACGGACATACCCTTGCCCAAGCGCGCCGGGTAG

TCCAACGCTACGCCCAAGATCCTAACTCCGAATACCGGCTGAAA

AGCGAAGCCGAGAAACACCTCACATCCATCAACGAGCTCCGCGT

ACAGATACTCCTCGAACAACTCCCCGTTGATGCCCTACGCATGG

CTACCGACCACCGCCTGCGCTTTGGATCCCTCGATTCCATCCAC

GTCGCAACCGTCGCCGACGTCCTAAAAACACACACCTCCATCCT

CACCACCGTGCAAGGTATCGGCGCCCAAACCGCGGGGCGGATGA

AAGCCGCAGCAGAAACACTCAAACAAGAAGCACTACGCCGCCAA

AACACCTCCATCGGCGACGAACCTACCCAACCCGCCATGCGTCT

AATCAACGTGCTGGCCCGCTTCGACCAAACCGAAACCATCACGC

CCGAAGAACGCGCCCGCCGCACCCGCGTCATCGACTACGTAGAA

CACATACCCCCAAGCCTCGACCCCTACATCGTCATCAACCCAGC

AACGCCTGAGTTCAACAACTTCACCGACGACCTCCGCTGGATCG

ACGCAA ACCCCAACCTCTTCCACCCACAAACAATCACCACCCC

ACCCGCCGACATCTGGGACGACTACATCTCCCGTCCCGCTCACT

ACCAAGGCCTGCTAGCCACGCTGCTCGGCCGCGACATCGAAGGC

GCAGACGAACTCCTCGACGCCACCACCCTCCAAAAAATCAGAGA

CCTCACCCTCGACAAAACTCA TCTCACCGACCTCCACCTCC G

CGGATACCA ATCATTCGGCGCCCGCTTCGCCATCATCCAAAAG

AAAACCCTCCTCGGCGACGACATGGGACTCGGCAAAACAGTCCA

AGCCCTCTCCGCAGCTGCACACCTTGCCGCCACCGAAAAAGACT

-continued

TCCGCACCCTCGTCGTCGTACCCGCATCCGTCATTGTTAACTGG

ACCCGCGAATGCAAACGCTTCCTCAACCTCCCCGTATTCATCGC

CCACGGAGACAACAAACAAGACGCCATCAACGCCTGGTCTAACA

CCAACGGAATCGCAATCTGCACCTACGACGGCGTCCGCACCATG

GACATCCCCGCGCCGGGTCTGGTCATTGCCGATGAAGCCCACCT

GATCAAAAACCCCTCCACCAAACGCACCCAAGCACTGCGCAAAC

TTATCGACGCCGCCCCATACACCCTTCTGATGACCGGCACACCA

CTAGAAAACAAAGTGGAAGAGTTTGTAAATCTCGTGCGCTACAT

CCAACCGGAGCTGATCACCCGTGGCATGTCCAAAATGCAGGCCG

AGAATTTCCGCGAGCGCATCGCACCAGCCTATCTGCGCAGAAAT

CAAGCTGATGTGCTTGACGAACTCCCAGAGCGCACCGACTCCAT

CGACTGGATCGACCTCACCCCAGAAGACCGCAGCGCCTACGACG

ACCAAGTCCGCCAAGGCAGCTGGATGGGCATGCGCCGCTCCGCC

ATGCTCTCACCAACACCACGCCTAACTTCCGCAAAAATGCAACG

CATCCTAGAACTCTTCGAAGAAGCAGAAGAACACGGCCGCAAAG

CCCTCATCTTCACCTACTTCCTCGACGTCCTCGACGAACTGGAA

AAGCATCTAGGCGAGCGCGTCATCGGCCGCATTTCCGGCGACGT

GCCAGCCACCAAGCGCCAATTGCTTGTCGACGCCCTGTCCCACT

CCAAACCCGGATCCGCCCTCATTGCCCAAATCACCGCCGGGGGA

GTAGGCCTAAACATCCAATCCGCGAGCCTATGCATTATTTGTGA

ACCTCAAGTAAAGCCAACCATCGAACAGCAGGCCGTCGCCCGAG

TCCACCGCATGGGCCAAACCGCCACCGTCCAAGTCCACCGACTC

ATCGGCGACGAAACCGCAGACGAACGCATGCTAGAAATCCTGGC

AGGCAAAACTCACGTCTTCGACGTCTACGCCCGGCTATCTGAAA

CCGCAGAGATTCCAGATGCTGTGGATATCACTGAATCACAGCTG

GCAGCACGGGTTATTGATGAGGAGCGTGCACGGTTAGGGCTTAC

TGAATCCACTGGCCCTAAAGATGAAGAAACGGCCTTAAGCTAG

SEQ ID NO: 30: NCgl1575$^{A1775T}$ ORF sequence:
ATGGCAGAATCAAACGCTATGGACCGGGCACAAATCTCTGCACT

GCTAGATAGAGCACAGCACACAATCAACCTTGCCGAACAAGCAA

ACAACGTGCTCCGACTGTTGAAAACACCCGGAACGGCCACAGTA

GGGGACAACGGGACACTCGGCACCGATACCTATCTGATCCCATC

CCGCAACATCACCTGGCCTGACAACCTGTATGTCAACGTCTTTC

TAGACGGCATGAATGCAGAAGCCACCCTTACCGATTACGTCGCA

TCAGTCGCTTCGATCCCACGCCTATGCCAGATCATCAACGAGGG

CCAAGGCGGCATGTTCCGCAGACTATTCAACCCCACCAAGGTCC

AAGCCGGCGACCAAGCTGTCTTCGACCTCATGGTCAAACTCGAC

GAGATTTCATCTACCACCCACGAAGTCTCCCGCATGCTCGAGGG

CGTCCACGCTGCCCGCACCCGCCAACAACAAGGCGTTGCACTTT

TCCCAGGTATTCATGGAGTGGGAGAGCGCTACATCGAACGCGCA

CAACAGGTACTCGCCTCAGCCCTCGGTATCGCTGGATTCGGTGC

-continued

CGAACCCTGGGACGGACATACCCTTGCCCAAGCGCGCCGGGTAG

TCCAACGCTACGCCCAAGATCCTAACTCCGAATACCGGCTGAAA

AGCGAAGCCGAGAAACACCTCACATCCATCAACGAGCTCCGCGT

ACAGATACTCCTCGAACAACTCCCCGTTGATGCCCTACGCATGG

CTACCGACCACCGCCTGCGCTTTGGATCCCTCGATTCCATCCAC

GTCGCAACCGTCGCCGACGTCCTAAAAACACACACCTCCATCCT

CACCACCGTGCAAGGTATCGGCGCCCAAACCGCGGGGCGGATGA

AAGCCGCAGCAGAAACACTCAAACAAGAAGCACTACGCCGCCAA

AACACCTCCATCGGCGACGAACCTACCCAACCCGCCATGCGTCT

AATCAACGTGCTGGCCCGCTTCGACCAAACCGAAACCATCACGC

CCGAAGAACGCGCCCGCCGCACCCGCGTCATCGACTACGTAGAA

CACATACCCCCAAGCCTCGACCCCTACATCGTCATCAACCCAGC

AACGCCTGAGTTCAACAACTTCACCGACGACCTCCGCTGGATCG

ACGCAA ACCCCAACCTCTTCCACCCACAAACAATCACCACCCC

ACCCGCCGACATCTGGGACGACTACATCTCCCGTCCGCTCACT

ACCAAGGCCTGCTAGCCACGCTGCTCGGCCGCGACATCGAAGGC

GCAGACGAACTCCTCGACGCCACCACCCTCCAAAAAATCAGAGA

CCTCACCCTCGACAAAACTCA TCTCACCGACCTCCACCTCC G

CGGATACCA ATCATTCGGCGCCCGCTTCGCCATCATCCAAAG

AAAACCCTCCTCGGCGACGACATGGGACTCGGCAAAACAGTCCA

AGCCCTCTCCGCAGCTGCACACCTTGCCGCCACCGAAAAAGACT

TCCGCACCCTCGTCGTCGTACCCGCATCCGTCATTGTTAACTGG

ACCCGCGAATGCAAACGCTTCCTCAACCTCCCCGTATTCATCGC

CCACGGAGACAACAAACAAGACGCCATCAACGCCTGGTCTAACA

CCAACGGAATCGCAATCTGCACCTACGACGGCGTCCGCACCATG

GACATCCCCGCGCCGGGTCTGGTCATTGCCGATGAAGCCCACCT

GATCAAAAACCCCTCCACCAAACGCACCCAAGCACTGCGCAAAC

TTATCGACGCCGCCCCATTCACCCTTCTGATGACCGGCACACCA

CTAGAAAACAAAGTGGAAGAGTTTGTAAATCTCGTGCGCTACAT

CCAACCGGAGCTGATCACCCGTGGCATGTCCAAAATGCAGGCCG

AGAATTTCCGCGAGCGCATCGCACCAGCCTATCTGCGCAGAAAT

CAAGCTGATGTGCTTGACGAACTCCCAGAGCGCACCGACTCCAT

CGACTGGATCGACCTCACCCCAGAAGACCGCAGCGCCTACGACG

ACCAAGTCCGCCAAGGCAGCTGGATGGGCATGCGCCGCTCCGCC

ATGCTCTCACCAACACCACGCCTAACTTCCGCAAAAATGCAACG

CATCCTAGAACTCTTCGAAGAAGCAGAAGAACACGGCCGCAAAG

CCCTCATCTTCACCTACTTCCTCGACGTCCTCGACGAACTGGAA

AAGCATCTAGGCGAGCGCGTCATCGGCCGCATTTCCGGCGACGT

GCCAGCCACCAAGCGCCAATTGCTTGTCGACGCCCTGTCCCACT

CCAAACCCGGATCCGCCCTCATTGCCCAAATCACCGCCGGGGGA

-continued

GTAGGCCTAAACATCCAATCCGCGAGCCTATGCATTATTTGTGA

ACCTCAAGTAAAGCCAACCATCGAACAGCAGGCCGTCGCCCGAG

TCCACCGCATGGGCCAAACCGCCACCGTCCAAGTCCACCGACTC

ATCGGCGACGAAACCGCAGACGAACGCATGCTAGAAATCCTGGC

AGGCAAAACTCACGTCTTCGACGTCTACGCCCGGCTATCTGAAA

CCGCAGAGATTCCAGATGCTGTGGATATCACTGAATCACAGCTG

GCAGCACGGGTTATTGATGAGGAGCGTGCACGGTTAGGGCTTAC

TGAATCCACTGGCC CTAAAGATGA AGAAACGGCCTTAAGCTA

G

SEQ ID NO: 31: NCgl1575 wild-type coding
protein sequence:
MAESNAMDRAQISALLDRAQHTINLAEQANNVLRLLKTPGTATV

GDNGTLGTDTYLIPSRDQAVFDLMVKLDEISSTTHEVSRMLEGV

HAARTRQQQGVALFPGIHGVGERYIERAQQVLASALGIAGFGAE

PWDGHTLAQARRVVQRYAQDPNSEYRLKSEAEKHLTSINELRVQ

ILLEQLPVDALRMATDHRLRFGSLDSIHVATVADVLKTHTSILT

TVQGIGAQTAGRMKAAAETLKQEALRRQNTSIGDEPTQPAMRLI

NVLARFDQTETITPEERARRTRVIDYVEHIPPSLDPYIVINPAT

PEFNNFTDDLRWIDANPNLFHPQTITTPPADIWDDYISRPAHYQ

GLLATLLGRDIEGADELLDATTLQKIRDLTLDKTHLTDLHLRGY

QSFGARFAIIQKKTLLGDDMGLGKTVQALSAAAHLAATEKDFRT

LVVVPASVIVNWTRECKRFLNLPVFIAHGDNKQDAINAWSNTNG

IAICTYDGVRTMDIPAPGLVIADEAHLIKNPSTKRTQALRKLID

AAPYTLLMTGTPLENKVEEFVNLVRYIQPELITRGMSKMQAENF

RERIAPAYLRRNQADVLDELPERTDSIDWIDLTPEDRSAYDDQV

RQGSWMGMRRSAMLSPTPRLTSAKMQRILELFEE AEEHGRKAL

IFTYFLDVLDELEKHLGERVIGRISGDVPATKRQLLVDALSHSK

PGSALIAQITAGGVGLNIQSASLCIICEPQVKPTIEQQAVARVH

RMGQTATVQVHRLIGDETADERMLEILAGKTHVFDVYARLSETA

EIPDAVDIT ESQLAARVID EERARLGLTE STGPKDEETA L

S

SEQ ID NO: 32: NCgl1575^(Y592F) coding protein
sequence:
MAESNAMDRAQISALLDRAQHTINLAEQANNVLRLLKTPGTATV

GDNGTLGTDTYLIPSRNITWPDNLYVNVFLDGMNAEATLTDYVA

SVASIPRLCQIINEGQGGMFRRLFNPTKVQAGDQAVFDLMVKLD

EISSTTHEVSRMLEGVHAARTRQQQGVALFPGIHGVGERYIERA

QQVLASALGIAGFGAEPWDGHTLAQARRVVQRYAQDPNSEYRLK

SEAEKHLTSINELRVQILLEQLPVDALRMATDHRLRFGSLDSIH

VATVADVLKTHTSILTTVQGIGAQTAGRMKAAAETLKQEALRRQ

NTSIGDEPTQPAMRLINVLARFDQTETITPEERARRTRVIDYVE

HIPPSLDPYIVINPATPEFNNFTDDLRWIDANPNLFHPQTITTP

PADIWDDYISRPAHYQGLLATLLGRDIEGADELLDATTLQKIRD

-continued

```
LTLDKTHLTDLHLRGYQSFGARFAIIQKKTLLGDDMGLGKTVQA

LSAAAHLAATEKDFRTLVVVPASVIVNWTRECKRFLNLPVFIAH

GDNKQDAINAWSNTNGIAICTYDGVRTMDIPAPGLVIADEAHLI

KNPSTKRTQALRKLIDAAPFTLLMTGTPLENKVEEFVNLVRYIQ

PELITRGMSKMQAE NFRERIAPAY LRRNQADVLD ELPERTD

SIDWIDLTPEDRSAYDDQVRQGSWMGMRRSAMLSPTPRLTSAKM

QRILELFEE AEEHGRKALIFTYFLDVLDELEKHLGERVIGRIS

GDVPATKRQLLVDALSHSKPGSALIAQITAGGVGLNIQSASLCI

ICEPQVKPTIEQQAVARVHRMGQTATVQVHRLIGDETADERMLE

ILAGKTHVFDVYARLSETAEIPDAVDIT ESQLAARVID EERA

RLGLTE STGPKDEETA LS

SEQ ID NO: 57: wild-type promotor sequence:
ttcagggtag ttgactaaag agttgctcgc gaagtagcac ctgtcacttt tgtctcaaatattaaatcga atatcaatat atggtctgtt tattggaacg cgtcccagtg gctgagacgc atccgctaaa gccccaggaa ccctgtgcag aaagaaaaca ctcctctggc taggtagacacagtttataa aggtagagtt gagcgggtaa ctgtcagcac gtagatcgaa aggtgcacaaag SEQ ID NO: 58: mutated promotor sequence:

ttcagggtag ttgactaaag agttgctcgc gaagtagcac ctgtcacttt tgtctcaaatattaaatcga atatcaatat atggtctgtt tattggaacg cgtcccagtg gctgagacg catccgctaaa gccccaggaa ccctgtgcag aaagaaaaca ctcctctggc taggtagacacagtttataa aggtataatt gagcgggtaa ctgtcagcac gtagatcgaa aggtgcacaaag
```

DEFINITION OF TERMS

In the present invention, the term "a bacterium with L-amino acid production capacity" refers to the ability to produce and accumulate L-amino acids of interest in culture medium and/or cells of the bacterium to the following extent, such that the bacterium producing L-amino acid can be collected when the bacterium is cultured in the culture medium. The bacterium with L-amino acid production capacity can be a bacterium that can accumulate L-amino acids of interest in culture medium and/or cells of the bacterium in an amount greater than that can be obtained by an unmodified strain.

Examples of L-amino acids include basic amino acids, such as L-lysine, L-ornithine, L-arginine, L-histidine, and L-citrulline; aliphatic amino acids, such as L-isoleucine, L-alanine, L-valine, L-leucine, and glycine; amino acids as hydroxy monoamino carboxylic acids, such as L-threonine and L-serine; cyclic amino acids, such as L-proline; aromatic amino acids, such as L-phenylalanine, L-tyrosine, and L-tryptophan; sulfur containing amino acids, such as L-cysteine, L-cystine, and L-methionine; acidic amino acids, such as L-glutamate and L-aspartate; and amino acids with amide groups in side chain, such as L-glutamine and L-asparagine. Specific examples of L-amino acids include L-glutamic acid, L-lysine, L-threonine, L-arginine, L-histidine, L-isoleucine, L-valine, L-leucine, L-phenylalanine, L-tyrosine, L-tryptophan, and L-cysteine. More specific examples of L-amino acids include L-glutamate, L-lysine, 1-threonine, and L-tryptophan. Yet more specific examples of L-amino acids include L-glutamate and L-lysine.

In the present invention, unless otherwise specified, the term "amino acid" refers to L-amino acid.

In the present invention, unless otherwise specified, the term "L-amino acid" refers to L-amino acid in free form, its salt or mixture thereof.

The term "unmodified strain" refers to a control strain that has not been modified in such a way that it has specific characteristics. That is, examples of unmodified strains include wild-type strains and parental strains.

The term "homology" refers to the percentage identity between two polynucleotides or two polypeptide modules. Sequence homology between one module and another module can be determined by using methods known in the art. For example, such sequence homology can be determined by BLAST algorithm.

The term "operably linking" refers to a functional linking between a regulatory sequence and a polynucleotide sequence, whereby the regulatory sequence controls the transcription and/or translation of the polynucleotide sequence. The regulatory sequence can be a strong promoter that can improve the expression level of polynucleotides. The regulatory sequence may be a promoter derived from a microorganism belonging to Corynebacterium genus or may be a promoter derived from other microorganisms. For example, the promoter may be a trc promoter, gap promoter, tac promoter, T7 promoter, lac promoter, trp promoter, araBAD promoter, or cj7 promoter.

The term "vector" refers to a polynucleotide construct that contains the regulatory sequence of a gene and the gene sequence and is configured to express a target gene in a suitable host cell. Alternatively, a vector can also refer to a polynucleotide construct, which contains sequences that can be used for homologous recombination, so that due to the vector introduced into the host cell, the regulatory sequence of the endogenous gene in the host cell's genome can be changed, or the target gene that can be expressed can be inserted into a specific site of the host's genome. In this regard, the vector used in the present invention may further comprise a selection marker to determine the introduction of the vector into the host cell or the insertion of the vector into the chromosome of the host cell. Selection markers may include markers conferring selectable phenotypes, such as drug resistance, auxotrophic type, resistance to cytotoxic agents, or expression of surface proteins. In environments treated with such selection agents, transformed cells can be selected because cells expressing only selection markers can survive or display different phenotypic traits.

As used herein, the term "transformation" refers to the introduction of polynucleotides into host cells, so that polynucleotides can be used as extragenomic elements or inserted into the genome of host cells for replication. The method of transforming the vectors used in the present invention may include a method of introducing nucleic acids into cells. In addition, as disclosed in the related technology, an electric pulse method can be implemented based on host cells.

Beneficial Effects

The invention finds that the product encoded by the gene has an impact on the production capacity of amino acids by weakening or knocking out the NCgl0609 gene or NCgl1575 gene. The recombinant strain is obtained by introducing point mutations into the coding sequence, or increasing the number of copies or overexpression of the gene. Compared with the wild-type strain, the obtained strain is conducive to the production of high concentrations of amino acids. Moreover, the recombinant strain was obtained by introducing point mutations into the promoter region of lysC gene. Compared with the unmutated strain, the obtained strain can also significantly improve the production of L-lysine, further to improve the generation efficiency, reduce the generation cost, and facilitate popularization and application.

THE DETAILED EMBODIMENTS

Hereinafter, the technical solution of the present invention will be further described in detail in combination with specific examples. It should be understood that the following examples are merely illustrative and explanatory of the invention and should not be construed as limiting the scope of protection of the invention. All technologies realized based on the above contents of the present invention are fallen into the scope of the present invention. Unless otherwise stated, all raw materials and reagents used in the following examples are commercially available products or can be prepared by known methods. All operations are known in the art, or performed according to the user manual of commercially available products.

In the following examples, the basic medium used for culturing the strains have the same composition, and sucrose, kanamycin or chloramphenicol etc. are added to such basic medium composition when necessary. The basic medium composition is as follows:

| Ingredients | Formulation |
| --- | --- |
| Sucrose | 10 g/L |
| Polypeptone | 10 g/L |
| Beef paste | 10 g/L |
| Yeast powder | 5 g/L |
| Urea | 2 g/L |
| Sodium chloride | 2.5 g/L |
| Agar powder | 20 g/L |

-continued

| Ingredients | Formulation |
| --- | --- |
| pH | 7.0 |
| Culture temperature | 32° C. |

The preparation and conditions of SSCP electrophoresis PAGE in the following examples are as follows.

| Ingredients | Amount (the final concentration of acrylamide is configured as 8%) |
| --- | --- |
| 40% acrylamide | 8 ml |
| ddH$_2$O | 26 ml |
| glycerol | 4 ml |
| 10*TBE | 2 ml |
| TEMED | 40 ul |
| 10% AP | 600 ul |
| Electrophoresis conditions | The electrophoresis tank is placed in ice and 1 × TBE buffer is used, voltage: 120 V, electrophoresis time: 10 h |

In the following examples, the fermentation medium and fermentation process of L-lysine are shown in Table 1 and 2 below:

TABLE 1

| L-lysine fermentation medium formulation | |
| --- | --- |
| Ingredients | formulation |
| Starch hydrolysis sugar | 30 g/L |
| Ammonium sulfate | 12 g/L |
| Magnesium sulfate | 0.87 g/L |
| Molasses | 20 g/L |
| Acidified corn steep liquor | 3 mL/L |
| Phosphoric acid | 0.4 mL/L |
| Potassium chloride | 0.53 g/L |
| Defoamer (2% GPE) | 4 mL/L |
| Ferrous sulfate | 120 mg/L |
| Manganese sulfate | 120 mg/L |
| Nicotinamide | 42 mg/L |
| Calcium pantothenate | 6.3 mg/L |
| Vitamin B1 | 6.3 mg/L |
| Copper and zinc salt solutions | 0.6 g/L |
| Biotin | 0.88 mg/L |

TABLE 2

| L-lysine fermentation control process | | | |
| --- | --- | --- | --- |
| Corrected DO100% | Temperature: 37° C., air velocity: 4 L/min, rotational speed: 1000 rpm, tank pressure: 0 mpa, calibrated after 5 min | | |
| Inoculation amount | 10% | Culture temperature ° C. | 37° C. |
| pH initial condition | pH 6.9 ± 0.05 | Dissolved oxygen DO | 10-30% |
| | Temperature 37° C., pH 6.9, tank pressure: 0 Mpa, air elocity: 3 L/min, rotational speed: 550 rpm | | |
| Full control | Full range control: 1. When the dissolved oxygen is less than 30%, the rotational speed is increased to 750 rpm → 800 rpm → air velocity 4 l/min → 850 rpm → 950 rpm in turn; 2. Fermentation for 6 h, tank pressure is increased by 0.01 Mpa; 12 h tank pressure is increased by 0.02 MPa → 0.03 MPa → 0.04 MPa → 0.05 Mpa | | |
| Residual sugar control | 0.1-0.2% before F12 h; After F12 h, in combination with DO, it is required to control residual sugar as 0.1-0.05% | | |
| Ammonia nitrogen control | 0.1-0.15 before F12 h; 0.15-0.25 in F12-F32 h; 0.1-0.15 after F32 h | | |
| Feed material | 25% ammonia, 70% concentrated sugar, 50% ammonium sulfate, 10% PGE | | |
| Fermentation cycle | About 48 h | | |

In the following examples, the fermentation medium and fermentation process of L-glutamate are shown in Table 3 and 4 below:

TABLE 3

L-glutamate fermentation medium formulation

| Reagent names | proportioning |
| --- | --- |
| glucose | 5.0 g/L |
| phosphoric acid | 0.38 g/L |
| Magnesium sulfate | 1.85 g/L |
| potassium chloride | 1.6 g/L |
| Biotin | 550 µg/L |
| Vitamin B1 | 300 µg/L |
| ferrous sulfate | 10 mg/L |
| Manganese sulfate | 10 g/dl |
| KH$_2$PO$_4$ | 2.8 g/L |
| Vitamin C | 0.75 mg/L |
| Vitamin B12 | 2.5 µg/L |
| P-aminobenzoic acid | 0.75 mg/L |
| Defoamer | 0.0015 ml/dl |
| betaine | 1.5 g/L |
| Cane Molasses | 7 ml/L |
| Corn steep liquor | 77 ml/L |
| Aspartic acid | 1.7 g/L |
| Hair powder | 2 g/L |

TABLE 4

L-glutamate fermentation control process

| | | | conditions | |
| --- | --- | --- | --- | --- |
| Periods | Revolutions | Air velocity | pressure | Culture temperature |
| 0 h | 400 rpm | 3 L/min | 0.05 MPA | 32.5° C. |
| OD 1.0 | 600 rpm | 5 L/min | 0.08 MPA | 37° C. |
| OD 1.4 | 700 rpm | 7 L/min | 0.11 MPA | 38° C. |
| 32 h~34 h | At the end of fermentation, 50~20% dissolved oxygen is used as the standard for increasing and decreasing air velocity in the control process | | | |
| PH | 0 h control: pH 7.0, 14 h control: pH 6.8 | | | |
| Feed sugar control | The concentration of feed sugar in the fermentation tank is 50~55%, and the residual sugar in the fermentation tank is controlled to be 0.5~1.0% | | | |

Example 1: Construction of the Transformed Vector pk18-NCgl0609$^{R334*}$ Containing the Coding Region of NCgl0609 Gene with Point Mutation Based on the genome sequence of *Corynebacterium glutamicum* ATCC13032 published by NCBI, two pairs of primers for amplifying the coding region sequence of NCgl0609 gene were designed and synthesized. Point mutation was introduced into the coding region of NCgl0609 gene (SEQ ID NO: 1, and the corresponding amino acid sequence encoding the proteins is SEQ ID NO: 3) in the background of strain YP97158 [Depositary No.: CGMCC No. 12856, Depositary date: Aug. 16, 2016, Depositary unit: Institute of Microbiology, Chinese Academy of Sciences, No. 3, Yard. 1, Beichen West Road, Chaoyang District, Beijing, Tel: 010-64807355, recorded in Chinese patent application CN106367432A (the filing date: Sep. 1, 2016, and the publication date: Feb. 1, 2017), and it is confirmed via sequencing that the wild type NCgl0609 gene was retained in the chromosome of the strain] by means of allelic replacement, and thus the nucleotide sequence of NCgl0609 gene at position 1000 was changed from C to T (SEQ ID NO: 2), and the corresponding amino acid sequence encoding proteins at position 334 was changed from arginine to a terminator (SEQ ID NO: 4: NCgl0609$^{R334*}$). The primers were designed as follows (synthesized by Shanghai Invitrogen Company):

```
P1:
                                    (SEQ ID NO: 5)
5' CAGTGCCAAGCTTGCATGCCTGCAGGTCGACTCTAG

GGACGGCAACGTACATAAC3';

P2:
                                    (SEQ ID NO: 6)
5' GTTGCCGGTGAGTCAAACAGTCATTTTGC 3';

P3:
                                    (SEQ ID NO: 7)
5' GCAAAATGACTGTTTGACTCACCGGCAAC 3';
and P4:
                                    (SEQ ID NO: 8)
5' CAGCTATGACCATGATTACGAATTCGAGCTCGGTACCC

GCGGCTG GAAATGTGGAG3'.
```

Construction method: *Corynebacterium glutamicum* ATCC13032 was used as the template, and primers P1 and P2, P3 and P4 were used, respectively, for PCR amplification. PCR System: 10×Ex Taq Buffer 5 µL, dNTP Mixture (each 2.5 mM) 4 µL, Mg$^{2+}$ (25 mM) 4 µL, primers (10 pM) each 2 µL, Ex Taq(5 U/µL) 0.25 µL, total volume 50 µL. The PCR amplification was carried out as follows: pre-denaturation for 5 min at 94° C., (denaturation for 30 s at 94° C., annealing for 30 s at 52° C., extension for 40 s at 72° C., 30 cycles), and over extension for 10 min at 72° C., and then two DNA fragments containing the coding region of NCgl0609 gene in sizes of 698 bp and 648 bp respectively (NCgl0609 Up and NCgl0609 Down) were obtained. After the two DNA fragments were separated and purified via agarose gel electrophoresis, the two DNA fragments as templates were amplified into 1317 bp fragments by overlap PCR with P1 and P4 as primers.

PCR system: 10×Ex Taq Buffer 5 µL, dNTP Mixture (each 2.5 mM) 4 µL, Mg$^{2+}$ (25 mM) 4 µL, primers (10 pM) each 2 µL, Ex Taq(5 U/µL) 0.25 µL, total volume 50 µL. The PCR amplification was carried out as follows: pre-denaturation for 5 min at 94° C., (denaturation for 30 s at 94° C., annealing for 30 s at 52° C., extension for 60 s at 72° C., 30 cycles), and over extension for 10 min at 72° C. This DNA fragment resulted in the change of cytosine (C) at position 1000 in the coding region of YP97158 NCgl0609 gene into thymine (T), and finally resulted in the 334th amino acid encoding the protein changed from arginine (R) to a terminator. This DNA fragment was purified via agarose gel electrophoresis, and was linked with the pK18mobsacB plasmid (purchased from Addgene company, double enzyme digested with Xbal I/BamH I, respectively) which was double enzyme digested and then purified with NEBuilder enzyme (purchased from NEB company) at 50° C. for 30 min, and a positive vector pk18-NCgl0609$^{R334*}$ was obtained from the monoclone grown after the transformation of the linked product by per identification, and this plasmid contained a kanamycin resistance marker. The vector pk18-NCgl0609$^{R334*}$ with correct enzyme digestion was sent to the sequencing company for sequencing and identification, and the vector pk18-NCgl0609$^{R334*}$ containing correct point mutation (C-T) was stored for use.

Example 2: Construction of an Engineered Strains of NCgl0609$^{R334*}$ Containing Point Mutation Construction method: the allelic replacement plasmid pk18-NCgl0609$^{R334*}$ was transformed into L-lysine production strain YP97158 by electric shock (See WO2014121669A1 for its construction method; it is confirmed by sequencing that the coding region of wild type NCgl0609 gene is reserved in the chromosome of the strain). The single colony produced by culturing was identified by primer P1 and universal primer M13R, and the strain that can amplify bands in size of 1375 bp was a positive strain. The positive strain was cultured on the medium containing 15% sucrose, the single colony produced by culturing was cultured on the medium containing kanamycin and the medium without kanamycin, respectively, and the strains that grew on the medium without kanamycin but did not grow on the medium containing kanamycin were further identified by PCR with the following primers (synthesized by Shanghai Invitrogen Company):

```
P5:
                                  (SEQ ID NO: 9)
5' CTAGCCGGTTCCAGTCAG 3';
and P6:
                                  (SEQ ID NO: 10)
5' GGACGTCTGTTCACCATTG 3'.
```

The above PCR amplification product was 264 bp, which was denatured at 95° C. for 10 min and subjected to ice bath for 5 min followed by sscp electrophoresis (the plasmid pk18-NCgl0609$^{R334*}$ amplification fragment was used as the positive control, YP97158 amplification fragment was used as the negative control, and the water was used as the blank control). Due to different fragment structures and electrophoresis positions, the strains whose electrophoresis positions are different from those of negative control fragments and are consistent with those of positive control fragments are the strains with successful allelic replacement. The NCgl0609 fragment of the positive strain was subjected to PCR amplification using primer P5/P6, and was linked to PMD19-T vector for sequencing. Through sequence alignment, the strain with mutation (C-T) of base sequence was the positive strain with successful allelic replacement, and was named as YPL-4-041.

Example 3: Construction of Engineering Strains Overexpressing NCgl0609 and NCgl0609$^{R334*}$ Genes in Genome Based on the genome sequence of wild type *Corynebacterium glutamicum* ATCC13032 published by NCBI, three pairs of primers for amplifying the upstream and downstream homologous arm fragments and the coding region and promoter region sequences of NCgl0609 and NCgl0609$^{R334*}$ gene were designed and synthesized, and NCgl0609 or NCgl0609$^{R334*}$ gene was introduced into strain YP97158 by way of homologous recombination.

Primers were designed as follows (synthesized by Shanghai Invitrogen Company):

```
P7:
                                  (SEQ ID NO: 11)
5' CAGTGCCAAGCTTGCATGCCTGCAGGTCGACTCTAG

AATGCGTTCTG GACTGAGG 3';

P8:
                                  (SEQ ID NO: 12)
5' CAGTGCCAAGCTTGCATGCCTGCAGGTCGACTCTAG

AATGCGTTCTG GACTGAGG 3';

P9:
                                  (SEQ ID NO: 13)
5' CATCTGTTCTCGGTGCACCAGCTGCGAGGATCATC

TC 3';

P10:
                                  (SEQ ID NO: 14)
5' GATTTAATTGCGCCATCTGATTCTGGCAACAACTC

CTTCCTTGACC 3';

P11:
                                  (SEQ ID NO: 15)
5' GGTCAAGGAAGGAGTTGTTGCCAGAATCAGATGGC

GCAATTA AATC AAG 3';
and

P12:
                                  (SEQ ID NO: 16)
5' CAGCTATGACCATGATTACGAATTCGAGCTCGGT

ACCCGCTATGACACCTTCAACGGATC 3'.
```

Construction method: *Corynebacterium glutamicum* ATCC13032 or YPL-4-041 was used as template, respectively, for PCR amplification with primers P7/P8, P9/P10, P11/P12, to obtain the upstream homologous arm fragment of 768 bp, NCgl0609 or NCgl0609$^{R334*}$ gene and its promoter fragment of 1626 bp and the downstream homologous arm fragment of 623 bp. After the completion of PCR reaction, the three amplified fragments were electrophoretically recovered using a column DNA gel recovery kit, respectively. The recovered three fragments were linked with the pK18mobsacB plasmid (purchased from Addgene Company, double enzyme digested with Xbal I/BamH I, respectively) which was double enzyme digested and then purified with NEBuilder enzyme (purchased from NEB Company) at 50° C. for 30 minutes, and a positive integrated plasmid was obtained from the monoclone grown after the transformation of the linked product by per identification. This plasmid contained a kanamycin resistance marker, and the recombinant with plasmid integrated into the genome can be obtained through kanamycin screening.

PCR system: 10×Ex Taq Buffer 5 µL, dNTP Mixture (each 2.5 mM) 4 µL, Mg$^{2+}$ (25 mM) 4 µL, primers (10 pM) each 2 µL, Ex Taq(5 U/µL) 0.25 µL, total volume 50 µL. The PCR amplification was carried out as follows: pre-denaturation for 5 min at 94° C., denaturation for 30 s at 94° C., annealing for 30 s at 52° C., extension for 60 s at 72° C. (30 cycles), and over extension for 10 min at 72° C. The correctly sequenced integrated plasmid was electrotransformed into the L-lysine production strain YP97158. The single colony produced by culturing was identified by PCR with primers P13/P14. The strain that amplified fragment with 1317 bp by PCR was a positive strain, and the strain without fragment by amplified was original strain. The positive strain was cultured on the medium containing 15% sucrose, and the single colony produced by culturing was further identified by PCR with primers P15/P16. The bacteria amplifying fragment of 1352 bp were positive strains with NCgl0609 or NCgl0609$^{R334*}$ gene integrated into the YP97158 genome, which were named YPL-4-042 (without mutation site) and YPL-4-043 (with mutation site).

```
P13:
                                    (SEQ ID NO: 17)
5' TCCAAGGAAGATACACGCC 3';

P14:
                                    (SEQ ID NO: 18)
5' CGAAATGGAAGTTGTGCG 3';

P15:
                                    (SEQ ID NO: 19)
5' CGATGATGCCGATTACCTC 3';

P16:
                                    (SEQ ID NO: 20)
5' CGTTGGAATCTTGCGTTG 3'.
```

Example 4: Construction of Engineering Strains Overexpressing NCgl0609 or NCgl0609$^{R334*}$ Genes in Plasmid Based on the genome sequence of wild type *Corynebacterium glutamicum* ATCC13032 published by NCBI, a pair of primers for amplifying the coding region and promoter region sequences of NCgl0609 or NCgl0609$^{R334*}$ gene were designed and synthesized. The primers were designed as follows (synthesized by Shanghai Invitrogen Company):

```
P17:
                                    (SEQ ID NO: 21)
5'GCTTGCATGCCTGCAGGTCGACTCTAGAGGATCCCC

CAGCTGCGAGG A TCATCTC 3';
and

P18:
                                    (SEQ ID NO: 22)
5'ATCAGGCTGAAAATCTTCTCTCATCCGCCAAAAC

CAACAACTCCTTCCTTGACC3'.
```

Construction method: *Corynebacterium glutamicum* ATCC13032 and YPL-4-041 were used as template, respectively, for PCR amplification with primers P17/P18 to obtain NCgl0609 and NCgl0609$^{R334*}$ genes and their promoter fragments of 1582 bp. The amplified products were subjected to electrophoresis and purified using a column DNA gel recovery kit. The recovered DNA fragment and a shuttle plasmid pXMJ19 recovered by EcoR I enzyme digestion were linked at 50° C. with NEBuilder enzyme (purchased from NEB) for 30 min, and the positive overexpression plasmids pXMJ19-NCgl0609 and pXMJ19-NCgl0609$^{R334*}$ were obtained from the monoclones grown after the transformation of the linker products by per identification with primer M13, and then these plasmids were sent to sequencing. Because the plasmid contained a chloramphenicol resistance marker, chloramphenicol can be used to screen whether the plasmid was transformed into the strain.

PCR system: 10×Ex Taq Buffer 5 µL, dNTP Mixture (each 2.5 mM) 4 µL, Mg$^{2+}$ (25 mM) 4 µL, primers (10 pM) each 2 µL, Ex Taq(5 U/µL) 0.25 µL, total volume 50 µL. The PCR amplification was carried out as follows: pre-denaturation for 5 min at 94° C., denaturation for 30 s at 94° C., annealing for 30 s at 52° C., extension for 60 s at 72° C. (30 cycles), and over extension for 10 min at 72° C.

The correctly sequenced pXMJ19-NCgl0609 and pXMJ19-NCgl0609$^{R334*}$ plasmids were electrotransformed into the L-lysine production strain YP97158, respectively. The single colony produced by culturing was identified by PCR with primers M13F/P18. The strains amplifying fragment with 1585 bp by PCR were positive strains, which was named YPL-4-044 (without mutation site) and YPL-4-045 (with mutation site).

Example 5: Construction of Engineered Strains with NCgl0609 Gene Deleted in Genome Based on the genome sequence of *Corynebacterium glutamicum* ATCC13032 published by NCBI, two pairs of primers for amplifying the fragments at two ends of the coding region of NCgl0609 gene were designed and synthesized, as upstream and downstream homologous arm fragments The primers were designed as follows (synthesized by Shanghai Invitrogen Company):

```
P19:
                                    (SEQ ID NO: 23)
5' CAGTGCCAAGCTTGCATGCCTGCAGGTCGACTCTAG

AATGAA TGG GATGGGTCG 3';
and

P20:
                                    (SEQ ID NO: 24)
5' CATCATCGGTTACTCTGGCCGAAATGGAAGTTGTGCG 3';

P21:
                                    (SEQ ID NO: 25)
5' CGCACAACTTCCATTTCGGCCAGAGTAACCGATGATG 3';

P22:
                                    (SEQ ID NO: 26)
5'CAGCTATGACCATGATTACGAATTCGAGCTCGGTACCC

TCAACAACTCCTCCTTGACC3'.
```

Construction method: *Corynebacterium glutamicum* ATCC13032 was used as template for PCR amplification with primers P19/P20 and P21/P22, respectively, to obtain upstream homologous arm fragment of 661 bp and downstream homologous arm fragment of 692 bp. Then primers P19/P22 were used for OVERLAP PCR to obtain the whole homologous arm fragment of 1334 bp. The amplified products were subjected to electrophoresis and purified using a column DNA gel recovery kit. The recovered DNA fragments were linked with the pK18mobsacB plasmid (purchased from Addgene Company, double enzyme digested with Xbal I/BamH I, respectively) which were double enzyme digested and then purified with NEBuilder enzyme (purchased from NEB Company) at 50° C. for 30 minutes.

Positive knockout vector pK18-ΔNCgl0609 were obtained from the monoclones grown after the transformation of the linker products by per identification with primer M13, and then these plasmids were sent to sequencing. The plasmid contained kanamycin resistance as a screening marker.

PCR system: 10×Ex Taq Buffer 5 μL, dNTP Mixture (each 2.5 mM) 4 μL, $Mg^{2+}$ (25 mM) 4 μL, primers (10 pM) each 2 μL, Ex Taq(5 U/μL) 0.25 μL, total volume 50 μL.

The PCR amplification was carried out as follows: pre-denaturation for 5 min at 94° C., denaturation for 30 s at 94° C., annealing for 30 s at 52° C., extension for 90 s at 72° C. (30 cycles), and over extension for 10 min at 72° C.

The correctly sequenced knockout plasmid pK18-ΔNCgl0609 was electrotransformed into lysine producing strain YP97158, and the single colony produced by culturing was identified by PCR with the following primers (synthesized by Shanghai Invitrogen Company):

```
P23:
                                (SEQ ID NO: 27)
5' AATGAATGG GATGGGTCG 3';
and P24:
                                (SEQ ID NO: 28)
5' CAACAACT CCT TCCTTGACC 3'.
```

The strains simultaneously amplifying 1334 bp and 1788 bp bands by the above PCR were positive strains, and the strains only amplifying 1788 bp band were original strains. After screening on the 15% sucrose medium, the positive strains were cultured on the medium containing kanamycin and the medium without kanamycin, respectively. The strains that grew on the medium without kanamycin but did not grow on the medium containing kanamycin were further identified by PCR using primers P23/P24. The strains amplifying 1334 bp band were the positive strains whose NCgl0609 gene coding region was knocked out. Again, the positive strain NCgl0609 fragment was PCR amplified with primers P23/P24 and linked to PMD19-T vector for sequencing. The correctly sequenced strain was named YPL-4-046.

Example 6: L-Lysine Fermentation Experiment

The strains constructed from Examples 2-5 and the original strain YP97158 were performed a fermentation experiment in the BLBIO-5GC-4-H fermentation tank (purchased from Shanghai Bailun Biotechnology Co., Ltd.) with the culture medium shown in Table 1 and the control process shown in Table 2. Each strain was repeated three times, and the results are shown in Table 5.

TABLE 5

| Results of L-lysine fermentation experiment | | |
|---|---|---|
| Strains | L-Lysine production (g/100 ml) | OD(660 nm) |
| YP97158 | 18.9 | 37.3 |
| YPL-4-041 | 19.3 | 38.1 |
| YPL-4-042 | 19.2 | 37.8 |
| YPL-4-043 | 19.5 | 38.4 |
| YPL-4-044 | 19.4 | 37.7 |
| YPL-4-045 | 19.7 | 38.3 |
| YPL-4-046 | 18.0 | 36.8 |

The results are as shown in Table 5. Point mutation $NCgl0609^{R334*}$ and overexpression of NCgl0609 gene coding region in Corynebacterium glutamicum contribute to the increase of L-lysine production and growth rate, while weakening or knocking out the gene is not conducive to the accumulation of L-lysine, and will reduce the growth rate of the strain.

Example 7: Introduction of NCgl0609 Gene Overexpression in Glutamate Production Strain, or Point mutation $NCgl0609^{R334*}$ and overexpression in the coding region of NCgl0609 gene, and preformation of fermentation experiments According to the methods of Examples 1-5, using the same primers and experimental conditions, Corynebacterium ATCC13869 was used as the starting bacterium, and the bacterium of ATCC 13869 was used as expression bacterium to obtain the glutamate production engineering strains YPG-013 containing point mutated $NCgl0609^{R334*}$, the glutamate production engineering strains YPG-014 and YPG-015 overexpressing NCgl0609 and $NCgl0609^{R334*}$ genes in the genome, the glutamate production engineering strains YPG-016 and YPG-017 overexpressing NCgl0609 and $NCgl0609^{R334*}$ genes in the plasmid, and the glutamate production engineering strain YPG-018 that lacks NCgl0609 gene in the genome.

The strains constructed in Examples and the original strain were performed a fermentation experiment (with bacterium of ATCC 13869 as expression bacterium) in the BLBIO-5GC-4-H fermentation tank (purchased from Shanghai Bailun Biotechnology Co., Ltd.) with the culture medium shown in Table 3 and the control process shown in Table 4. Each strain was repeated three times, and the results are shown in Table 6.

TABLE 6

| Results of L-glutamate fermentation experiment | | |
|---|---|---|
| Strains | L-glutamate production (g/l) | OD(660 nm) |
| ATCC13869 | 101.0 | 42.3 |
| YPG-013 | 103.5 | 43.4 |
| YPG-014 | 103.9 | 42.8 |
| YPG-015 | 103.2 | 43.7 |
| YPG-016 | 103.6 | 42.6 |
| YPG-017 | 103.8 | 43.6 |
| YPG-018 | 98.5 | 40.5 |

The results are as shown in Table 6. Point mutation $NCgl0609^{R334*}$ and overexpression of NCgl0609 gene coding region in Corynebacterium glutamicum contribute to the increase of L-glutamate production and growth rate, while weakening or knocking out the gene is not conducive to the accumulation of L-glutamic acid, and will reduce the growth rate of the strain.

Example 8: Construction of Transformation Vector pK18-NCgl1575^{A1775T} Containing the Coding Region of NCgl1575 Gene with Point Mutation Based on the genome sequence of wild type Corynebacterium glutamicum ATCC13032 published by NCBI, two pairs of primers for amplifying the coding region sequence of NCgl1575 gene were designed and synthesized. Point mutation was introduced into the coding region of NCgl1575 gene (SEQ ID NO:29) in the background of strain YP97158 (it was confirmed by sequencing that wild type NCgl1575 gene was retained in the chromosome of the strain) by means of allelic replacement.

The corresponding amino acid sequence encoding the proteins was SEQ ID NO:31, and the nucleotide sequence of NCgl1575 gene at position 1775 was changed from A to T (SEQ ID NO:30: NCgl1575$^{A1775T}$) and in the corresponding amino acid sequence encoding the proteins at position 592 was changed from tyrosine to phenylalanine (SEQ ID NO:32: NCgl1575 Y592F).

Primers were designed as follows (synthesized by Shanghai Invitrogen Company):

```
P1':
                              (SEQ ID NO: 33)
5'CAGTGCCAAGCTTGCATGCCTGCAGGTCGACTCTAG

TGCGTTCGTCTGCGGTTTCG 3';

P2':
                              (SEQ ID NO: 34)
5' ATCGACGCCGCCCCATTCACCCTTCTGATG 3';

P3':
                              (SEQ ID NO: 35)
5' CATCAGAAGGGTGAATGGGCGGCGTCGAT 3';
and P4':
                              (SEQ ID NO: 36)
5'CAGCTATGACCATGATTACGAATTCGAGCTCGGTACCC

AAGCCTCGACCCCTACATC 3'.
```

Construction method: *Corynebacterium glutamicum* ATCC13032 was used as template for PCR amplification with primers P1' and P2', P3' and P4', respectively.

PCR system: 10×Ex Taq Buffer 5 μL, dNTP Mixture (each 2.5 mM) 4 μL, Mg$^{2+}$ (25 mM) 4 μL, primers (10 pM) each 2 μL, Ex Taq(5 U/μL) 0.25 μL, total volume 50 μL.

The PCR amplification was carried out as follows: predenaturation for 5 min at 94° C., denaturation for 30 s at 94° C., annealing for 30 s at 52° C., extension for 40 s at 72° C. (30 cycles), and over extension for 10 min at 72° C. Two DNA fragments containing NCgl1575 gene coding region in sizes of 766 bp and 759 bp, respectively, were obtained (NCgl1575 Up and NCgl1575 Down).

After separation and purification of the above two DNA fragments by agarose gel electrophoresis, the above two DNA fragments were used as templates, and P1' and P4' were used as primers, to amplify a fragment in length of about 1495 bp by overlap PCR.

PCR system: 10×Ex Taq Buffer 5 μL, dNTP Mixture (each 2.5 mM) 4 μL, Mg$^{2+}$ (25 mM) 4 μL, primers (10 pM) each 2 μL, Ex Taq(5 U/μL) 0.25 μL, total volume 50 μL.

The PCR amplification was carried out as follows: predenaturation for 5 min at 94° C., denaturation for 30 s at 94° C., annealing for 30 s at 52° C., extension for 90 s at 72° C. (30 cycles), and over extension for 10 min at 72° C.

This DNA fragment (NCgl1575$^{A1775T}$) resulted in the change of adenine (A) at position 1775 in the coding region of YP97158 NCgl1575 gene into thymine (T), and finally resulted in the change of amino acid at position 592 of the coding protein from tyrosine (Y) to phenylalanine (F).

The NCgl1575$^{A1775T}$ separated and purified by agarose gel electrophoresis and the pK18mobsacB plasmid (purchased from Addgene) recovered by Xba I enzyme digestion were assembled with the NEBuider recombination system to obtain vector pK18-NCgl1575$^{A1775T}$, and the plasmid contained a kanamycin resistance marker. The vector pK18-NCgl1575$^{A1775T}$ was sent to the sequencing company for sequencing and identification, and the vector pK18-NCgl1575$^{A1775T}$ containing the correct point mutation (A-T) was stored for use.

Example 9: Construction of Engineering Strains Containing NCgl1575$^{A1775T}$ with Point Mutation Construction method: The allelic replacement plasmid pK18-NCgl1575$^{A1775T}$ was transformed into L-lysine production strain YP97158 by electric shock. The single colony produced by culturing was identified by primer P1' and universal primer M13R, respectively. The strain that can amplify 1502 bp band was a positive strain. The positive strains were cultured on the medium containing 15% sucrose, and the single colony produced by culturing was cultured on the medium containing kanamycin and the medium without kanamycin, respectively. The strains that grew on the medium without kanamycin, but did not grow on the medium containing kanamycin were further identified by PCR with the following primers (synthesized by Shanghai Invitrogen Company):

```
P5':
                              (SEQ ID NO: 37)
5' CACATC AGCTTGATTT CTGC 3';
and P6':
                              (SEQ ID NO: 38)
5' GGTCATTGCC GATGAAGCCC 3'.
```

The above PCR amplification product was 256 bp, which was denatured at high temperature and subjected to ice bath, followed by sscp electrophoresis (the plasmid pK18-NCgl1575$^{A1775T}$ amplification fragment was used as the positive control, YP97158 amplification fragment was used as the negative control, and the water was used as the blank control). Due to different fragment structures and electrophoresis positions, the strains whose electrophoresis positions are different from those of negative control fragments and are consistent with those of positive control fragments are the strains with successful allelic replacement. The fragment of interest of the strains with successful allelic replacement was subjected to PCR amplification using primer P5' and P6' again, and was linked to PMD19-T vector for sequencing. Through sequence alignment, the sequence in which base sequence is mutated verifies that the allelic replacement of the strain is successful, and it is named YPL-4-023.

Example 10: Construction of Engineering Strains Overexpressing NCgl1575 or NCgl1575$^{A1775T}$ Gene in Genome Based on the genome sequence of wild type *Corynebacterium glutamicum* ATCC13032 published by NCBI, three pairs of primers for amplifying the upstream and downstream homologous arm fragments and the sequences of NCgl1575 or NCgl1575$^{A1775T}$ gene coding region and promoter region were designed and synthesized, and NCgl1575 or NCgl1575$^{A1775T}$ gene was introduced into strain YP97158 by homologous recombination.

Primer was designed as follows (synthesized by Shanghai Invitrogen Company):

```
P7':
                                        (SEQ ID NO: 39)
5' CAGTGCCAAGCTTGCATGCCTGCAGGTCGACTCTAGAATG

CGTTCTGGACTGAGG 3';

P8':
                                        (SEQ ID NO: 40)
5' GAAACGGCCTTAAGCTAGGTGCACCGAG AACAGATG 3';

P9':
                                        (SEQ ID NO: 41)
5' CATCTGTTCTCGGTGCAC CTAGCTTAAG GCCGTTTC 3';

P10':
                                        (SEQ ID NO: 42)
5' CTTGATTTAATTGCGCCATCAAGCTTTTCC CGCCCGGTT 3';

P11':
                                        (SEQ ID NO: 43)
5' AACCGGGCGG GAAAAGCTTGATGGCGCAATTAAATCAAG 3';
and P12':
                                        (SEQ ID NO: 44)
5'CAGCTATGACCATGATTACGAATTCGAGCTCGGTACCC GCTAT

GACACCTTCAACGGATC 3'.
```

Construction method: *Corynebacterium glutamicum* ATCC13032 or YPL-4-023 was used as templates, respectively, for PCR amplification with primers P7'/P8', P9'/P10', P11'/P12', to obtain upstream homologous arm fragment of 802 bp, NCgl1575 gene and its promoter fragment of 2737 bp, or NCgl1575$^{41775T}$ gene and its promoter fragment of 2737 bp, and downstream homologous arm fragment of 647 bp. Then, the above three amplified fragments (upstream homologous arm fragment, NCgl1575 gene and its promoter fragment, and downstream homologous arm fragment; or upstream homologous arm fragment, NCgl1575$^{41775T}$ gene and its promoter fragment, and downstream homologous arm fragment) were mixed as template for amplification with primers P7'/P12' to obtain integrated homologous arm fragment of 4111 bp.

After the completion of PCR reaction, the amplified product is electrophoretically recovered, and the 4111 bp DNA fragment required was recovered with a column DNA gel recovery kit (TIANGEN), and was linked with the shuttle plasmid PK18mobsacB recovered by Xba I enzyme digestion using NEBBuider recombination system, to obtain the integrated plasmid PK18mobsacB-NCgl1575 or PK18mobsacB-NCgl1575$^{41775T}$. The plasmid contained a kanamycin resistance marker, and the recombinant with plasmid integrated into the genome can be obtained through kanamycin screening.

PCR system: 10×Ex Taq Buffer 5 μL, dNTP Mixture (each 2.5 mM) 4 μL, Mg$^{2+}$ (25 mM) 4 μL, primers (10 pM) each 2 μL, Ex Taq(5 U/μL) 0.25 μL, total volume 50 μL.

The PCR amplification was carried out as follows: pre-denaturation for 5 min at 94° C., denaturation for 30 s at 94° C., annealing for 30 s at 52° C., extension for 180 s at 72° C. (30 cycles), and over extension for 10 min at 72° C.

The two integrated plasmids were electrotransformed into the L-lysine production strain YP97158, respectively, and the single colony produced by culturing was identified by PCR with primers P13'/P14'. The strain amplifying fragments in size of 1778 bp by PCR was a positive strain, the strain without fragments amplified was an original strain. The positive strains were screened on 15% sucrose medium and then cultured on the medium containing kanamycin and the medium without kanamycin, respectively. The strains that grew on the medium without kanamycin, but did not grow on the medium containing kanamycin were further identified by PCR with primers P15'/P16'. The bacteria amplifying fragment in size of 1756 bp were strains with NCgl1575 or NCgl1575$^{41775T}$ gene integrated into the YP97158 genome, which were named YPL-4-024 (without mutation site) and YPL-4-025 (with mutation site), respectively.

```
P13':
                                        (SEQ ID NO: 45)
   5' TCCAAGGAAGATACACGCC 3';

P14':
                                        (SEQ ID NO: 46)
   5' CTTCTGATGA CCGGCACACC 3';

P15':
                                        (SEQ ID NO: 47)
   5' TAGTCGATGA CGCGGGTGCG 3';
   and P16':
                                        (SEQ ID NO: 48)
   5' CGTTGGAATCTTGCGTTG 3'.
```

Example 11: Construction of Engineering Strains Overexpressing NCgl1575 or NCgl1575$^{41775T}$ Gene on Plasmid Based on the genome sequence of wild type *Corynebacterium glutamicum* ATCC13032 published by NCBI, a pair of primers for amplifying the coding region and promoter region sequences of NCgl1575 or NCgl1575$^{41775T}$ gene were designed and synthesized. The primers were design as follows (synthesized by Shanghai Invitrogen Company):

```
P17':
                                        (SEQ ID NO: 49)
5'GCTTGCATGCCTGCAGGTCGACTCTAGAGGATCCCC CTAGCT

TAAG GCCGTTTC 3';
and

P18':
                                        (SEQ ID NO: 50)
5'ATCAGGCTGAAAATCTTCTCTCATCCGCCAAAAC AAGCTTT

TCC CGCCCGGTT 3'
```

Construction method: ATCC13032 and YPL-4-023 were used as templates, respectively, for PCR amplification with primers P17'/P18', to obtain NCgl1575 or NCgl1575$^{41775T}$ gene and their promotor fragments of 2749 bp. The amplified products were recovered by electrophoresis. The desired 2749 bp DNA fragments were recovered by a column DNA gel recovery kit, and were linked with the shuttle plasmid pXMJ19 recovered by EcoR I enzyme digestion using the NEBuider recombination system to obtain the overexpression plasmids pXMJ19-NCgl1575 and pXMJ19-NCgl1575$^{41775T}$. Plasmids containing chloramphenicol resistance markers can be obtained through chloramphenicol screening and transformed into strains.

PCR system: 10×Ex Taq Buffer 5 μL, dNTP Mixture (each 2.5 mM) 4 μL, Mg$^{2+}$ (25 mM) 4 μL, primers (10 pM) each 2 μL, Ex Taq(5 U/μL) 0.25 μL, total volume 50 μL.

The PCR amplification was carried out as follows: pre-denaturation for 5 min at 94° C., denaturation for 30 s at 94°

C., annealing for 30 s at 52° C., extension for 120 s at 72° C. (30 cycles), and over extension for 10 min at 72° C.

The plasmids pXMJ19-NCgl1575 and pXMJ19-NCgl1575$^{41775T}$ were electrotransformed into the L-lysine production strain YP97158, respectively. The single colony produced by culturing was identified by PCR with primers M13 (−48) and P18'. The single colony amplifying fragment in size of 2752 bp by PCR was transformed strains which were named YPL-4-026 (without mutation site) and YPL-4-027 (with mutation site).

Example 12: Construction of Engineering Strains with NCgl1575 Gene Deleted in Genome Based on the genome sequence of *Corynebacterium glutamicum* ATCC13032 published by NCBI, two pairs of primers for amplifying fragments at two ends of the coding region of NCgl1575 gene were synthesized as upstream and downstream homologous arm fragments. Primers were design as follows (synthesized by Shanghai Invitrogen Company):

```
P19':
                                    (SEQ ID NO: 51)
5'CAGTGCCAAGCTTGCATGCCTGCAGGTCGACTCTAGACCG

GCGCAG ATGCCAACGC 3';

P20':
                                    (SEQ ID NO: 52)
CCCAGAACTGAAGGTCTAATTGCCTAAGG CCGGAATT 3';

P21':
                                    (SEQ ID NO: 53)
AATTCCGGCCTTAGGCAATTAGACCTTC AGTTCTGGG 3';
and P22':
                                    (SEQ ID NO: 54)
5' CAGCTATGACCATGATTACGAATTCGAGCTCGGTACCC GCT

TGATGAA GGCTCCAG 3'.
```

*Corynebacterium glutamicum* ATCC13032 was used as a template for PCR amplification with primers P19'/P20' and P21'/P22', respectively, so as to obtain upstream homologous arm fragment of 775 bp and downstream homologous arm fragments of 807 bp. Then, they were subjected to overlap PCR with primers P19'/P22' to obtain a whole homologous arm fragment of 1545 bp. After the completion of PCR reaction, the amplified product was electrophoretically recovered, and the desired 1545 bp DNA fragment was recovered using a column DNA gel recovery kit, and was linked with shuttle plasmid pk18mobsacB recovered by Xba I enzyme digestion through the NEbuider recombination system to obtain knockout plasmid. The plasmid contained a kanamycin resistant marker.

The knockout plasmid was electrotransformed into a lysine producing strain YP97158, and the single colony produced by culturing was identified by PCR with the following primers (synthesized by Shanghai Invitrogen Company):

```
P23':
                                    (SEQ ID NO: 55)
5' ACCGGCGCAG ATGCCAACGC 3';
```

```
-continued
and

P24':
                                    (SEQ ID NO: 56)
5' GCTTGATGAA GGCTCCAG 3'.
```

The strains amplifying bands in size of 1471 bp and 4150 bp by above PCR were positive strains, and the strains only amplifying a band in size of 4150 were original bacteria. After screening on 15% sucrose medium, the positive strains were cultured on the medium containing kanamycin and the medium without kanamycin, respectively, and the strains that grew on the medium without kanamycin but did not grow on the medium containing kanamycin were further identified by PCR using primers P23'/P24'. The strain amplifying a band in size of 1471 bp was the engineering strain with the coding sequence of NCgl1575 gene deleted, which was named YPL-4-028.

Example 13: L-Lysine Fermentation Experiment

The strains constructed from Examples 9-12 and the original strain YP97158 were performed a fermentation experiment in the BLBIO-5GC-4-H fermentation tank (purchased from Shanghai Bailun Biotechnology Co., Ltd.) with the culture medium shown in Table 1 and the control process shown in Table 2. Each strain was repeated three times, and the results are shown in Table 7.

TABLE 7

| Results of L-Lysine fermentation experiment | | |
|---|---|---|
| Strains | L-lysine production (g/100 ml) | OD(660 nm) |
| YP97158 | 18.8 | 37.3 |
| YPL-4-023 | 19.6 | 36.8 |
| YPL-4-024 | 19.6 | 37.0 |
| YPL-4-025 | 19.8 | 35.5 |
| YPL-4-026 | 19.3 | 36.3 |
| YPL-4-027 | 19.7 | 37.2 |
| YPL-4-028 | 18.0 | 36.8 |

The results are as shown in Table 7. Overexpression of NCgl1575 gene in *Corynebacterium glutamicum*, or point mutation NCgl1575$^{41775T}$ and overexpression of NCgl1575 gene coding region are conducive to the increase of L-lysine production, while weakening or knocking out the gene is not conducive to the accumulation of L-lysine.

Example 14: Construction of a Transformation Vector pK18-PlysC$^{(G(−45)A,G(−47)T)}$ Containing the Promoter Region of lysC Gene with Point Mutation Based on the genome sequence of *Corynebacterium glutamicum* ATCC13032 published by NCBI, two pairs of primers for amplifying the sequences of lysC gene promoter region were designed and synthesized, and point mutation was introduced into the lysC gene promoter region (SEQ ID NO: 57) in the background of strain YP97158 by means of allelic replacement. The G at position −45 bp of lysC gene promoter region nucleotide sequence was changed to A, and the G at position −47 bp was changed to T (SEQ ID NO: 58). Primers were designed as follows (synthesized by Shanghai Invitrogen Company):

```
P1":
                                    (SEQ ID NO: 59)
5' CCGGAATTCG ACCAAGGATG AGGGCTTTG 3';
(EcoR I)
```

-continued

```
P2":
                                (SEQ ID NO: 60)
5' AGTTACCCGC TCAATTATAC CTTTATAAAC 3';

P3":
                                (SEQ ID NO: 61)
5' GTTTATAAAG GTATAATTGAGCGGGTAACT 3';
and P4":
                                (SEQ ID NO: 62)
5' ACATGCATGCGCGTACGCGAAGTGGCACAT 3'.
   (Sph I)
```

Construction method: *Corynebacterium glutamicum* ATCC13032 was used as a template for PCR amplification with primers P1" and P2", P3" and P4", respectively. PCR system: 10×Ex Taq Buffer 5 µL, dNTP Mixture (each 2.5 mM) 4 µL, $Mg^{2+}$ (25 mM) 4 µL, primers (10 pM) each 2 µL, Ex Taq(5 U/µL) 0.25 µL, total volume 50 µL. The PCR amplification was carried out as follows: pre-denaturation for 5 min at 94° C., denaturation for 30 s at 94° C., annealing for 30 s at 52° C., extension for 40 s at 72° C. (30 cycles), and over extension for 10 min at 72° C. Two DNA fragments with point mutation in size of 729 bp and 760 bp, respectively, were obtained (lysC promotor Up and lysC promotor Down fragments). After the above two DNA fragments were separated and purified by agarose gel electrophoresis, the purified two DNA fragments were used as templates, and P1" and P4" were used as primers to amplify a fragment with a length of about 1459 bp (Up Down fragment) by Overlap PCR. PCR system: 10×Ex Taq Buffer 5 µL, dNTP Mixture (each 2.5 mM) 4 µL, $Mg^{2+}$ (25 mM) 4 µL, primers (10 pM) each 2 µL, Ex Taq(5 U/µL) 0.25 µL, total volume 50 µL. The PCR amplification was carried out as follows: pre-denaturation for 5 min at 94° C., denaturation for 30 s at 94° C., annealing for 30 s at 52° C., extension for 90 s at 72° C. (30 cycles), and over extension for 10 min at 72° C. The above Up-Down fragment was separated and purified by agarose gel electrophoresis, and the fragment contained lysC gene promoter region and its upstream and downstream sequences, and both ends of the fragment contained EcoR I and Sph I enzyme digestion sites, respectively. This DNA fragment causes the change of nucleotide guanine (G) at position −45 bp in the promoter region of YP97158 lysC gene to adenine (A), and the nucleotide guanine (G) at position −47 bp to thymine (T). The fragment was purified and recovered after double enzyme digestion (EcoR I/Sph I), and was linked with the shuttle plasmid pK18mobsacB (purchased from Addgene) after the same double enzyme digestion (EcoR I/Sph I) to obtain an allelic replacement plasmid pK18-PlysC$^{(G(-45)A,G(-47)T)}$, which contained a Kanamycin resistance marker. The vector pK18-PlysC$^{(G(-45)A,G(-47)T)}$ was sent to the sequencing company for sequencing and identification, and the vector pK18-PlysC$^{(G(-45)A,G(-47)T)}$ containing the correct point mutation was stored for use.

Example 15: Construction of Engineering Strains Containing PlysC$^{(G(-45)A,G(-47)T)}$ with Point Mutation The allelic replacement plasmid pK18-PlysC$^{(G(-45)A,G(-47)T)}$ was transformed into L-lysine production strain YP97158 by electric shock. The single colony produced by culturing was identified by primer P1" and universal primer M13F, respectively, and the strains that can amplify a band in size of 1500 bp were positive strains. The positive strains were cultured on the medium containing 15% sucrose, and the single colony produced by culturing was cultured on the medium containing kanamycin and the medium without kanamycin, respectively; the strains that grew on the medium without kanamycin but did not grow on the medium containing kanamycin were further identified by PCR using the following primers (synthesized by Shanghai Invitrogen Company):

```
P5":
                                (SEQ ID NO: 63)
5' ATCAATATATGGTCTGTTTA 3';
and P6":
                                (SEQ ID NO: 64)
5' CTTGGTGGCAACGATCCGTT 3'
```

The above PCR amplification product was denatured at high temperature and subjected to ice bath followed by sscp electrophoresis (the plasmid pK18-PlysC$^{(G(-45)A,G(-47)T)}$ amplification fragment was used as the positive control, YP97158 amplification fragment was used as the negative control, and the water was used as the blank control). Due to different fragment structures and electrophoresis positions, the strains whose electrophoresis positions are different from those of negative control fragments and are consistent with those of positive control fragments are the strains with successful allelic replacement. The target fragment of the positive strain was amplified by PCR again, and linked to the PMD19-T vector for sequencing. Through sequence alignment, the sequence in which base sequence is mutated verifies that the allelic replacement of the strain is successful, and it is named YPL-4-009.

Example 16: L-Lysine Fermentation Experiment

The strain YPL-4-009 constructed in Example 15 and the original strain YP97158 were performed a fermentation experiment in the BLBIO-5GC-4-H fermentation tank (purchased from Shanghai Bailun Biotechnology Co., Ltd.) with the culture medium shown in Table 1 and the control process shown in Table 2. Each strain was repeated three times, and the results are shown in Table 8.

TABLE 8

| L-Lysine fermentation experiment results | | | |
| --- | --- | --- | --- |
| Strains | | L-Lysine production (g/100 ml) | Conversion rate (%) |
| YP97158 | batch 1 | 18.7 | 64.1 |
| | batch 2 | 18.8 | 64.0 |
| | batch 3 | 18.8 | 63.7 |
| | mean | 18.8 | 63.9 |
| YPL-4-009 | batch 1 | 21.0 | 64.7 |
| | batch 2 | 20.9 | 64.6 |
| | batch 3 | 20.9 | 64.7 |
| | mean | 20.9 | 64.7 |
| increased folds | | 11.17% | 1.25% |

The above conversion rate = total mass of lysine/total consumption of glucose *100%

The results are shown in Table 8. The point mutation PlysC$^{(G(-45)A,G(-47)T)}$ of lysC gene promoter in *Corynebacterium glutamicum* is contributive to the increase of the L-lysine production.

The embodiment of the invention has been described above. However, the present invention is not limited to the above embodiments. Any modification, equivalent replacement, improvement, etc. made within the spirit and principle
of the invention shall be included in the protection scope of
the invention.

---

What is claimed is:

1. A bacterium producing L-amino acid, comprising:

a polynucleotide sequence encoding the amino acid sequence shown in SEQ ID NO: 31 with a point mutation of tyrosine to phenylalanine at position 592; or the polynucleotide sequence shown in SEQ ID NO: 29 with a point mutation of adenine to thymine at position 1775, wherein the bacterium is *Corynebacterium glutamicum.*

2. The bacterium as claimed in claim 1, wherein the bacterium comprises the polynucleotide sequence shown in SEQ ID NO: 30.

3. The bacterium as claimed in claim 1, wherein the *Corynebacterium glutamicum* is YP97158 or ATCC 13869.

4. A method for producing L-amino acid, the method comprises culturing the bacterium of claim 1 and recovering L-amino acid from the culture.

5. A product comprising:

(I) a polynucleotide sequence encoding the amino acid sequence shown in SEQ ID NO: 31 with a point mutation of tyrosine to phenylalanine at position 592;

(II) a recombinant vector, wherein the recombinant vector comprises the polynucleotide sequence of said (I);

(III) a recombinant strain, wherein the recombinant strain comprises the polynucleotide sequence of said (I).

6. The product of claim 5, wherein the polynucleotide sequence encodes the amino acid sequence shown in SEQ ID NO: 32.

7. The product of claim 5, wherein the polynucleotide sequence is formed by a mutation of $1775^{th}$ base of the polynucleotide sequence shown in SEQ ID NO: 29.

8. The product of claim 7, wherein the mutation is a mutation of the $1775^{th}$ base of the polynucleotide sequence shown in SEQ ID NO: 29 from adenine (A) to thymine (T).

9. The product of claim 5, wherein the polynucleotide sequence is shown in SEQ ID NO: 30.

* * * * *